United States Patent
Ryu et al.

(10) Patent No.: US 10,724,039 B2
(45) Date of Patent: Jul. 28, 2020

(54) APTAMER AGAINST INSULIN RECEPTOR AND PHARMACEUTICAL COMPOSTION CONTAINING THE SAME

(71) Applicants: POSCO, Pohang-si, Gyeongsangbuk-do (KR); POSTECH ACADEMY-INDUSTRY FOUNDATION, Pohang-si, Gyeongsangbuk-do (KR)

(72) Inventors: Sung Ho Ryu, Pohang-si (KR); Na-Oh Yunn, Gongju-si (KR); Jong Hun Im, Seoul (KR); Ara Koh, Seoul (KR); Eun Ju Oh, Pohang-si (KR); Sehoon Park, Changwon-si (KR); Jiyoun Lee, Pohang-si (KR); Sung Key Jang, Pohang-si (KR); Seungmin Han, Pohang-si (KR); Youndong Kim, Goyang-si (KR)

(73) Assignees: Posco, Pohang-si, Gyeongsangbuk-do (KR); Postech Academy-Industry Foundation, Pohang-si, Gyeongsangbuk-do (KR)

( * ) Notice: Subject to any disclaimer, the term of this patent is extended or adjusted under 35 U.S.C. 154(b) by 92 days.

(21) Appl. No.: 15/746,654

(22) PCT Filed: May 3, 2016

(86) PCT No.: PCT/KR2016/004665
§ 371 (c)(1),
(2) Date: Jan. 22, 2018

(87) PCT Pub. No.: WO2017/018641
PCT Pub. Date: Feb. 2, 2017

(65) Prior Publication Data
US 2019/0032060 A1   Jan. 31, 2019

(30) Foreign Application Priority Data

Jul. 27, 2015   (KR) ........................ 10-2015-0106151

(51) Int. Cl.
| | |
|---|---|
| *C12N 15/11* | (2006.01) |
| *C12N 15/113* | (2010.01) |
| *A61K 31/711* | (2006.01) |
| *G01N 33/53* | (2006.01) |
| *C12N 15/115* | (2010.01) |
| *A61P 3/10* | (2006.01) |
| *A61K 31/7088* | (2006.01) |
| *A61K 38/28* | (2006.01) |
| *G01N 33/74* | (2006.01) |

(52) U.S. Cl.
CPC ...... *C12N 15/1138* (2013.01); *A61K 31/7088* (2013.01); *A61K 31/711* (2013.01); *A61K 38/28* (2013.01); *A61P 3/10* (2018.01); *C12N 15/115* (2013.01); *G01N 33/53* (2013.01); *G01N 33/74* (2013.01); *C12N 2310/16* (2013.01); *C12N 2310/335* (2013.01); *G01N 2333/62* (2013.01)

(58) Field of Classification Search
None
See application file for complete search history.

(56) References Cited

U.S. PATENT DOCUMENTS

| | | | |
|---|---|---|---|
| 2004/0110235 A1* | 6/2004 | Epstein | C07H 21/04 435/7.2 |
| 2012/0083521 A1 | 4/2012 | Sullenger et al. | |
| 2013/0059292 A1 | 3/2013 | Kim | |

FOREIGN PATENT DOCUMENTS

WO   2004-011680 A1   2/2004

OTHER PUBLICATIONS

Lollo et al, Beyond antibodies: New affinity reagents to unlock the proteome, Proteomics, 2014, 14: 638-644.*
International Search Report and Written Opinion dated Sep. 22, 2016 issued in International Patent Application No. PCT/KR2016/004665 (with English translation).
Sark, Ga-Young, "Selection of DNA Aptamer Switched on Signaling of Insulin Receptor by SELEX," The Korean Society for Biotechnology and Bioengineering International Symposium, Apr. 2015, No. P0814, p. 568.
Kim, Kiseok et al., "Efficient isolation and elution of cellular proteins using aptamer-mediated protein precipitation assay," Biochemical and Biophysical Research Communications, Apr. 24, 2014, vol. 448, No. 1, pp. 114-119.
Chang, Minhyeok et al., "Aptamer-based single-molecule imaging of insulin receptors in living cells," Journal of Biomedical Optics, May 2014, vol. 19, No. 5.
Yunn, Na-Oh et al., "Agonistic aptamer to the insulin receptor leads to biased signaling and functional selectivity through allosteric modulation," Nucleic Acids Research, Aug. 5, 2015, vol. 43, No. 16, pp. 1-13.

(Continued)

*Primary Examiner* — Ekaterina Poliakova-Georgantas
(74) *Attorney, Agent, or Firm* — Morgan, Lewis & Bockius LLP

(57) ABSTRACT

The present disclosure relates to a DNA aptamer which specifically binds to an insulin receptor, and a composition for treating diabetes and a composition for diagnosing diabetes which contain the same as an active ingredient, and the aptamer is characterized by being able to treat and diagnose diabetes more effectively than side effects caused by insulin such as increased incidence of cancer and atherosclerosis by having a different binding mechanism from existing insulin.

10 Claims, 20 Drawing Sheets
Specification includes a Sequence Listing.

(56) References Cited

OTHER PUBLICATIONS

Corbin, John A. et al., "Improved Glucose Metabolism In Vitro and In Vivo by an Allosteric Monoclonal Antibody That Increases Insulin Receptor Binding Affinity," PLOS One, Feb. 14, 2014, vol. 9, Issue 2, pp. 1-12.
Bhaskar, Vinay et al., "A Fully Human, Allosteric Monoclonal Antibody That Activates the Insulin Receptor and Improves Glycemic Control," Diabetes, vol. 61, May 2012, pp. 1263-1271.
Office Action issued in Korean Patent Application No. 2018-503571 dated Nov. 27, 2018, with English translation.

* cited by examiner

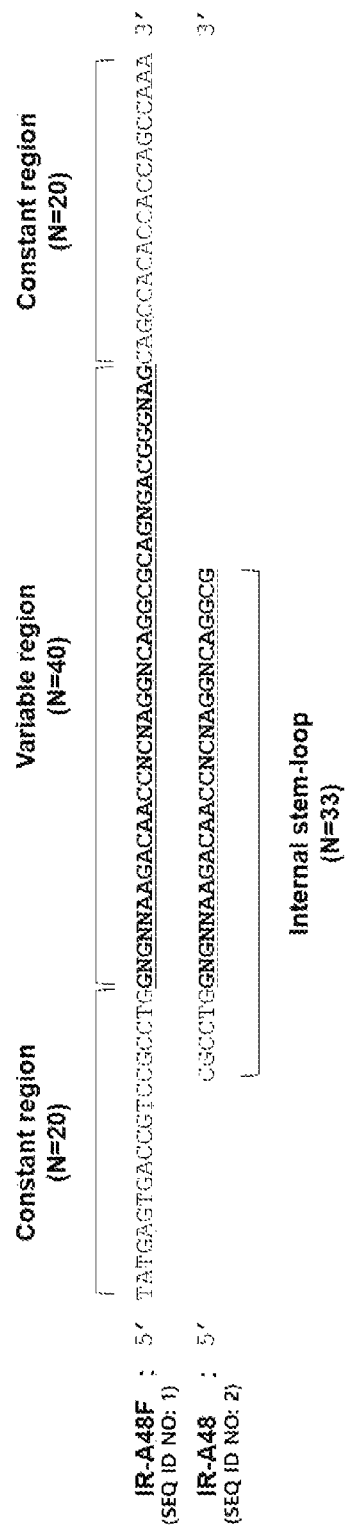

[FIG. 1b]
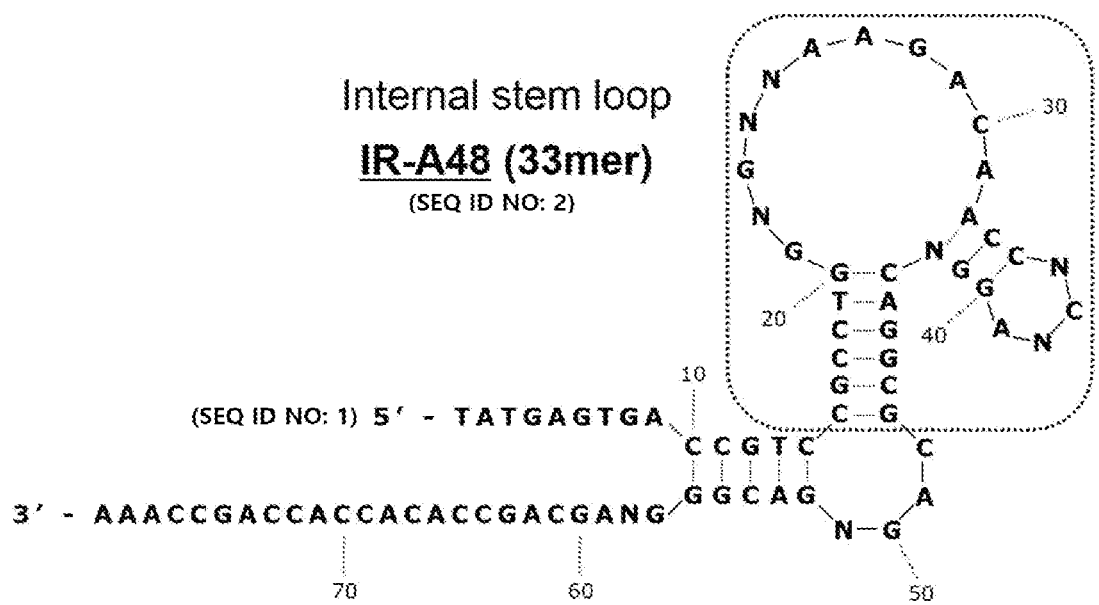
[FIG. 1c]
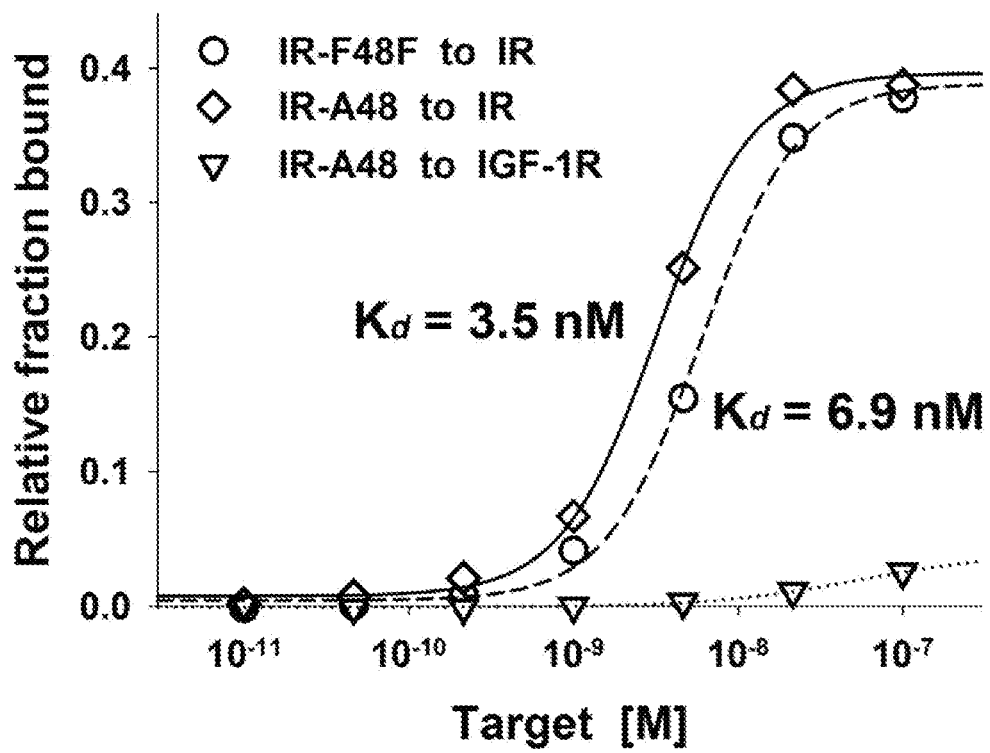

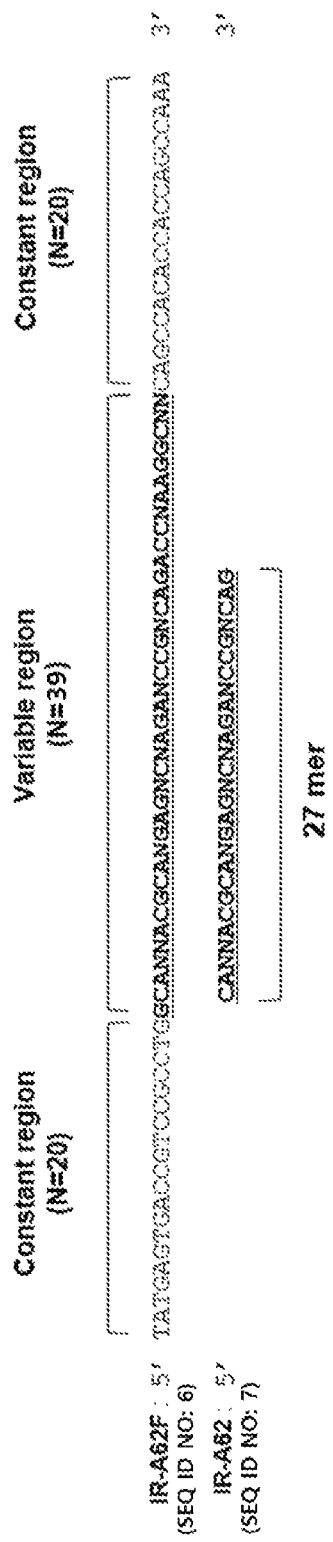
[FIG. 1d]

【FIG. 1e】
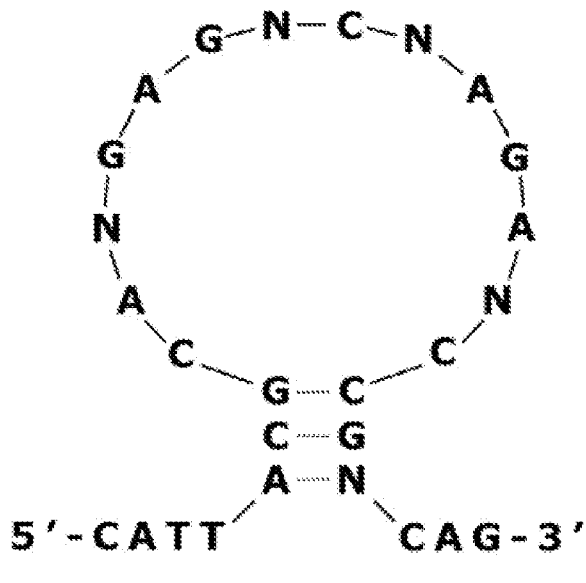
(SEQ ID NO: 7)
【FIG. 1f】
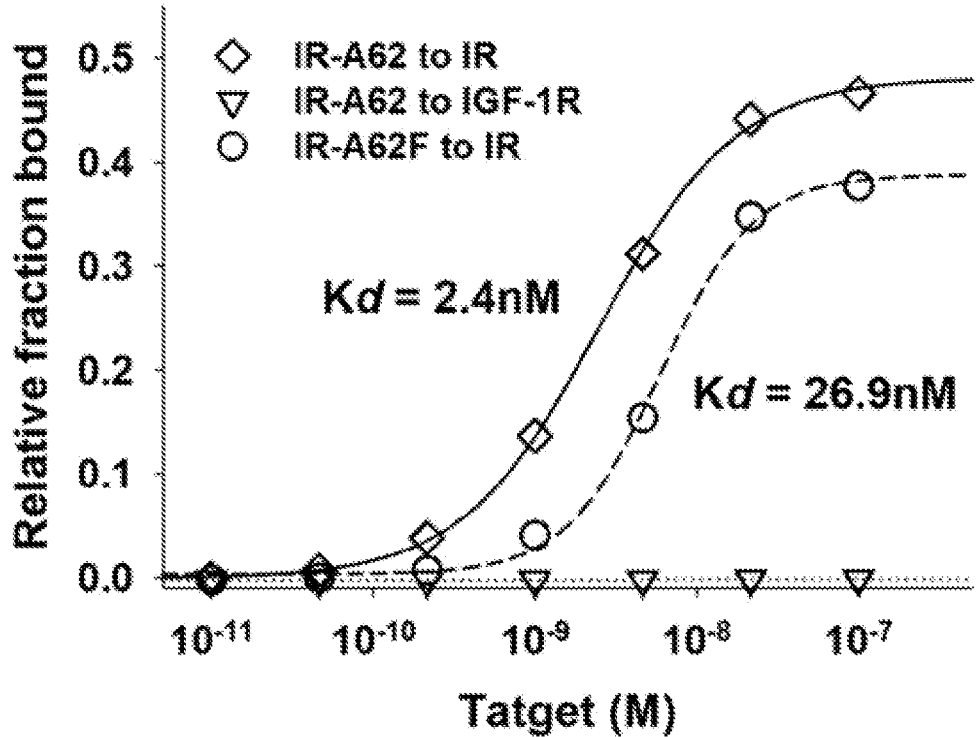

[FIG. 2a]
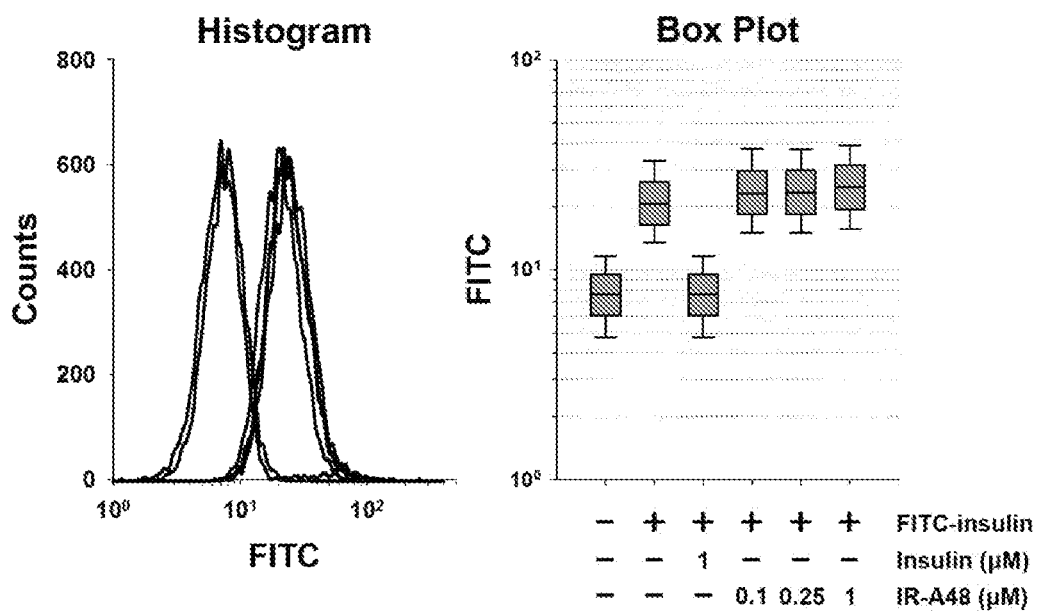
[FIG. 2b]
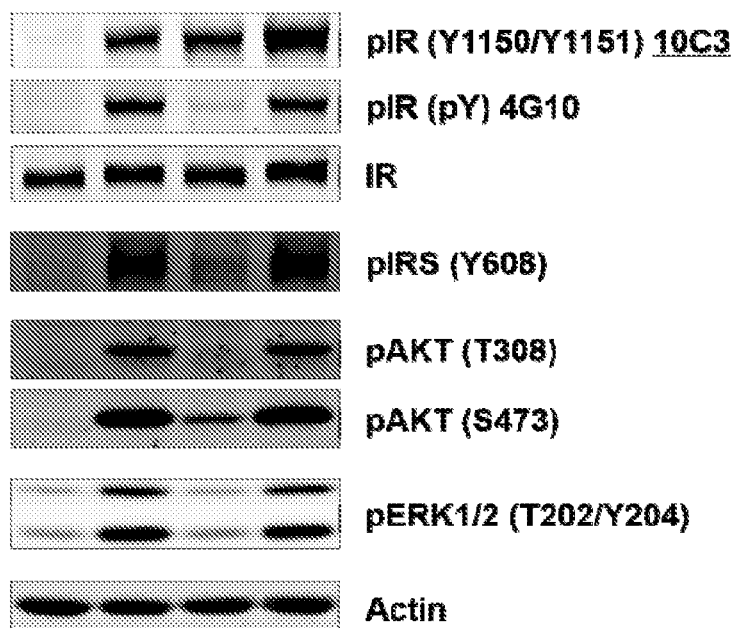

[FIG. 2c]
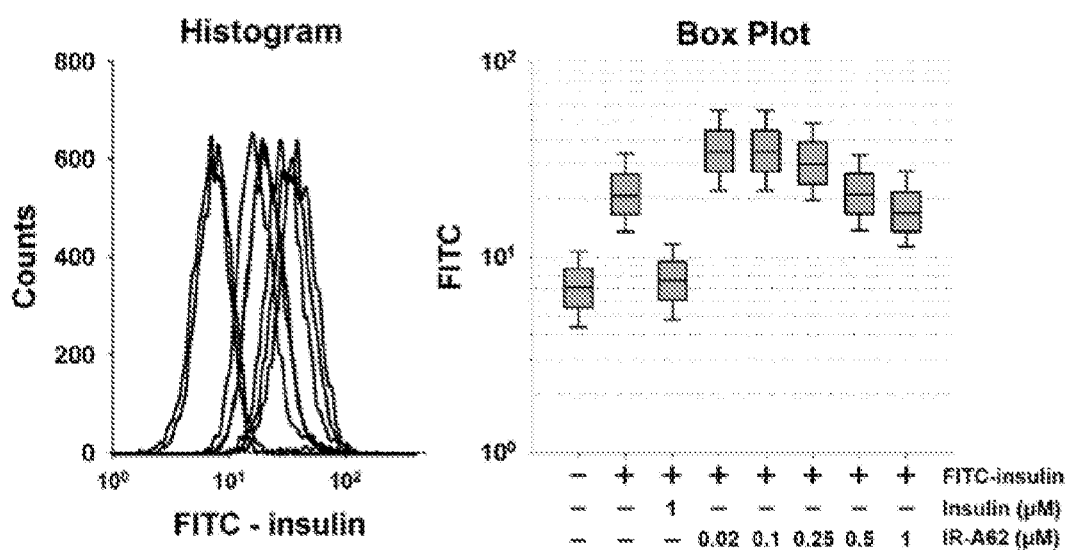

【FIG. 2d】
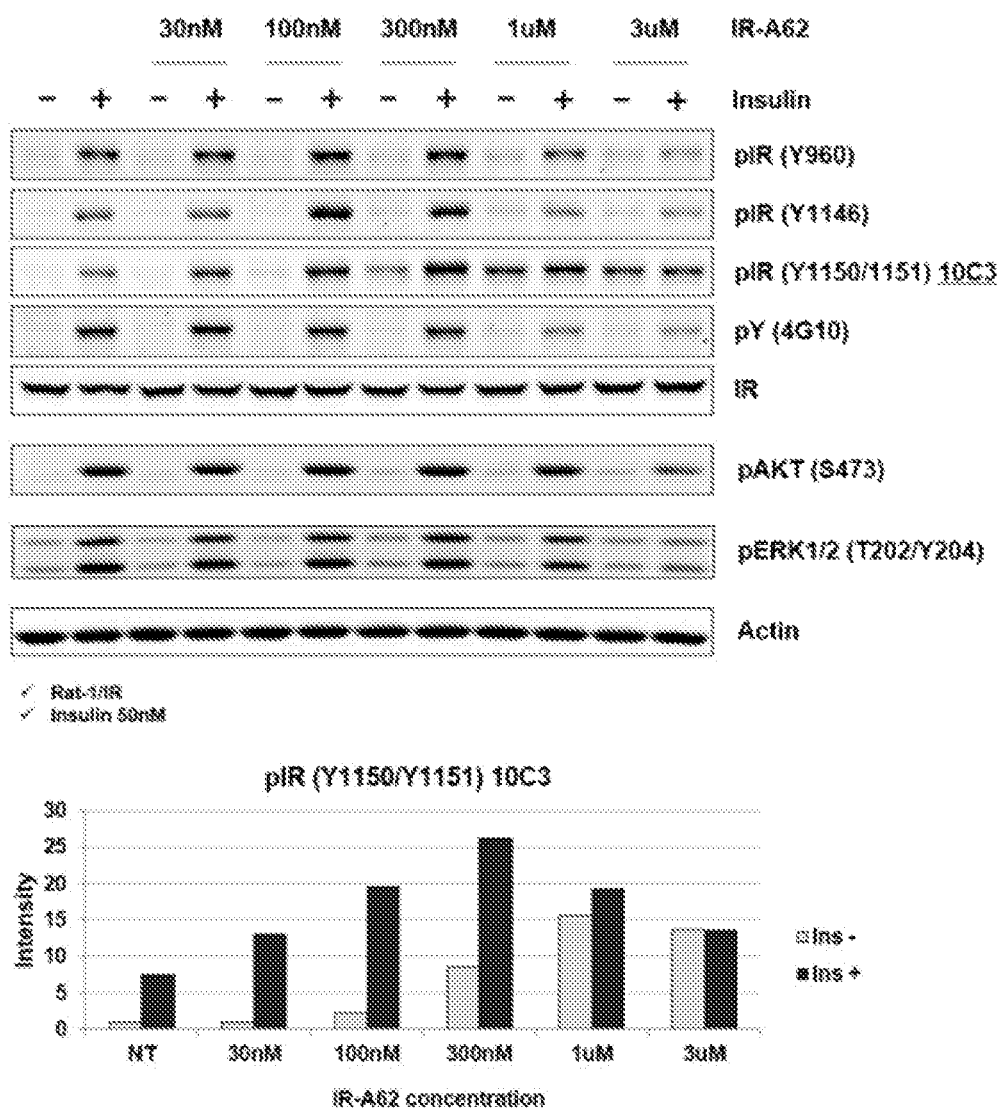

[FIG. 3a]
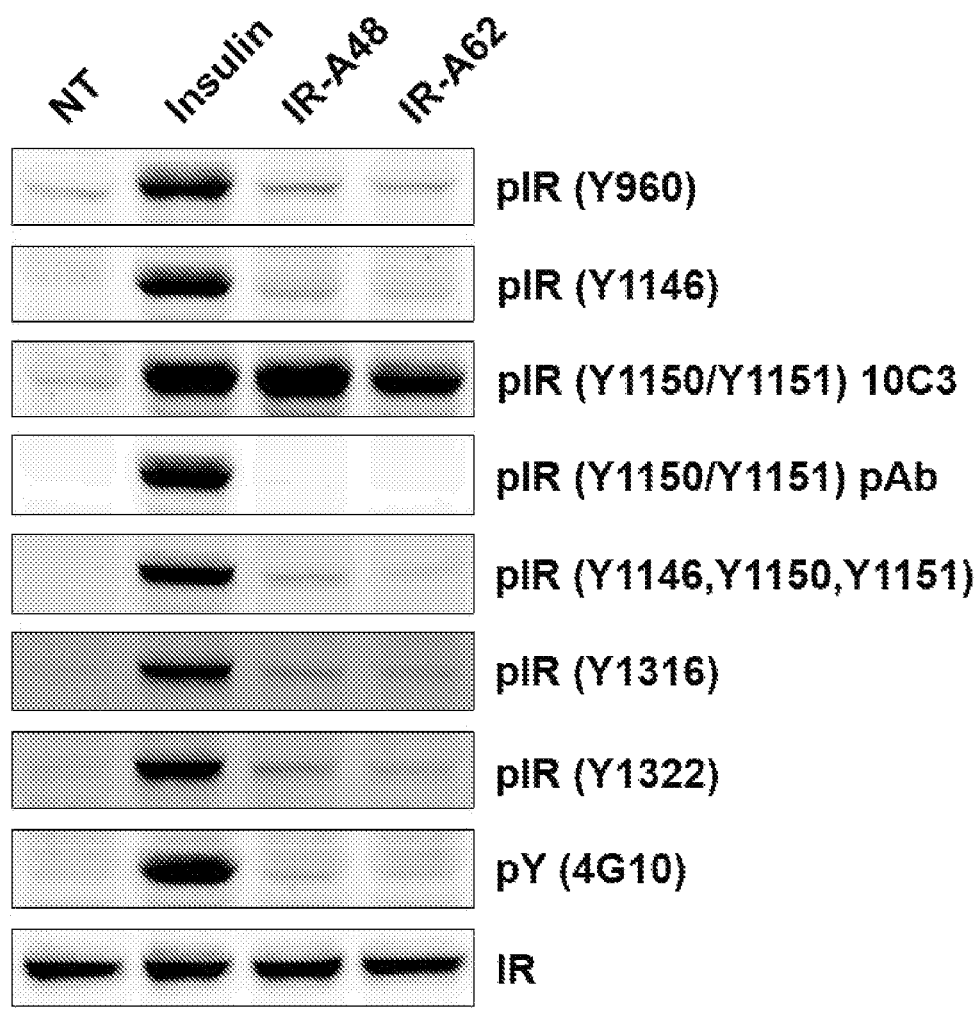

【FIG. 3b】
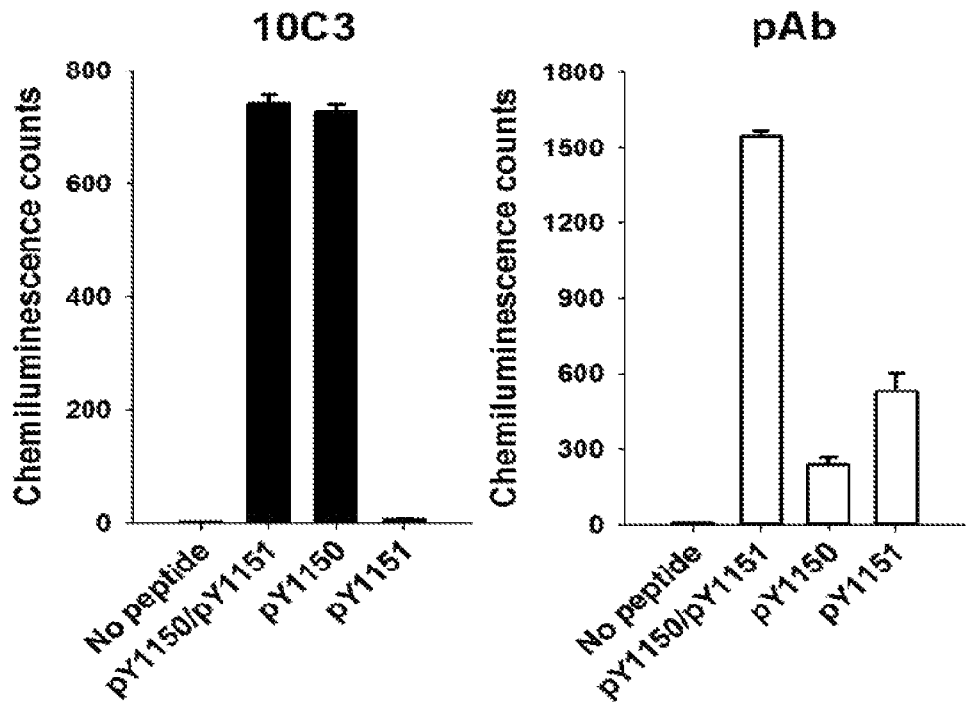
【FIG. 3c】
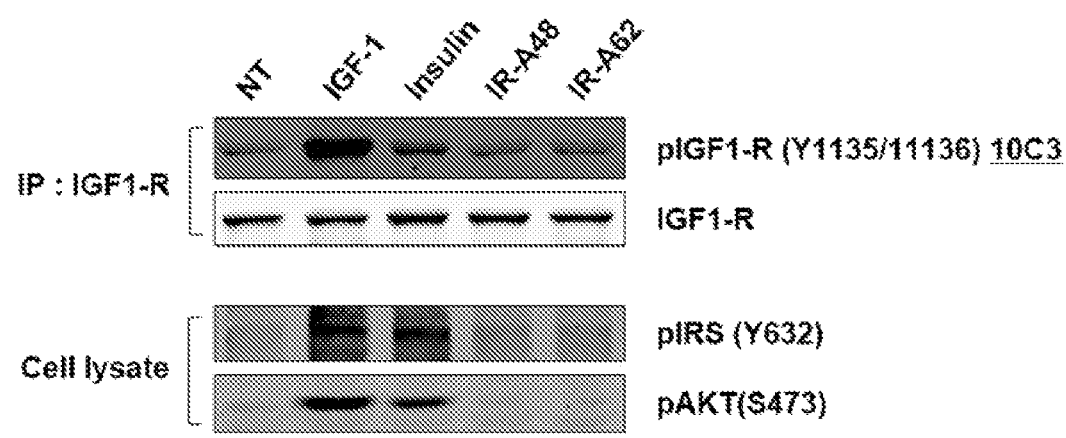

[FIG. 4a]
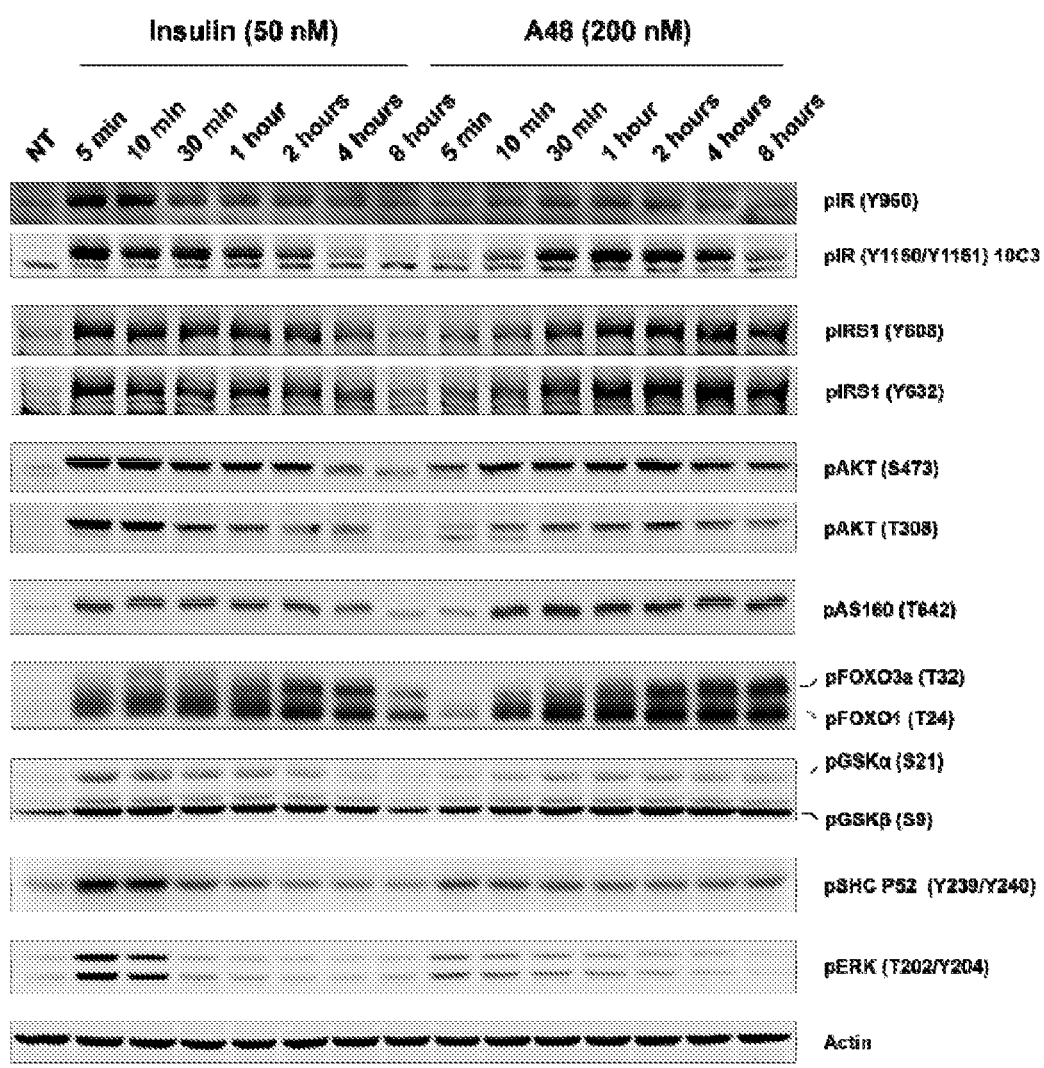

[FIG. 4b]
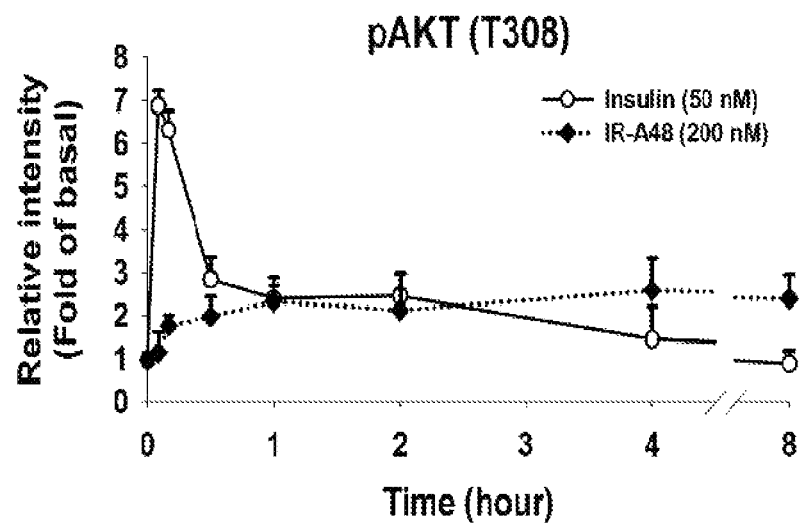
[FIG. 4c]
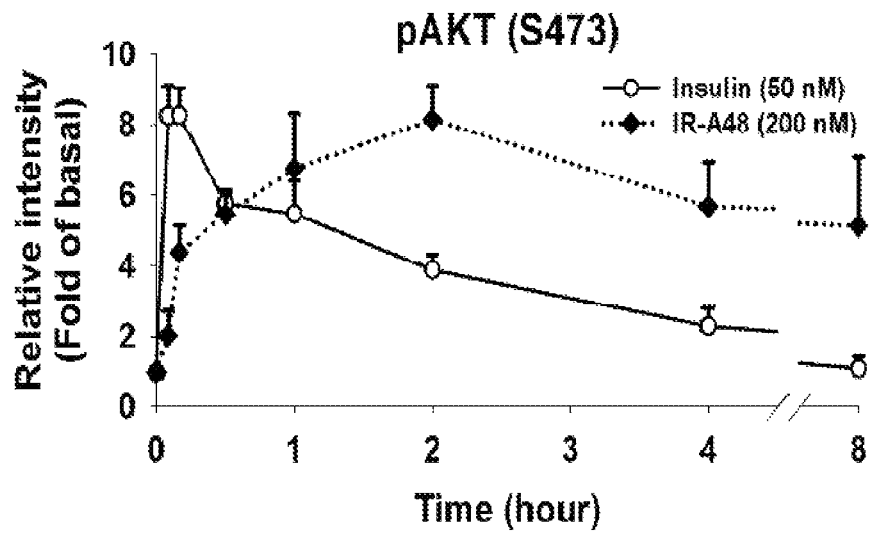

[FIG. 4d]
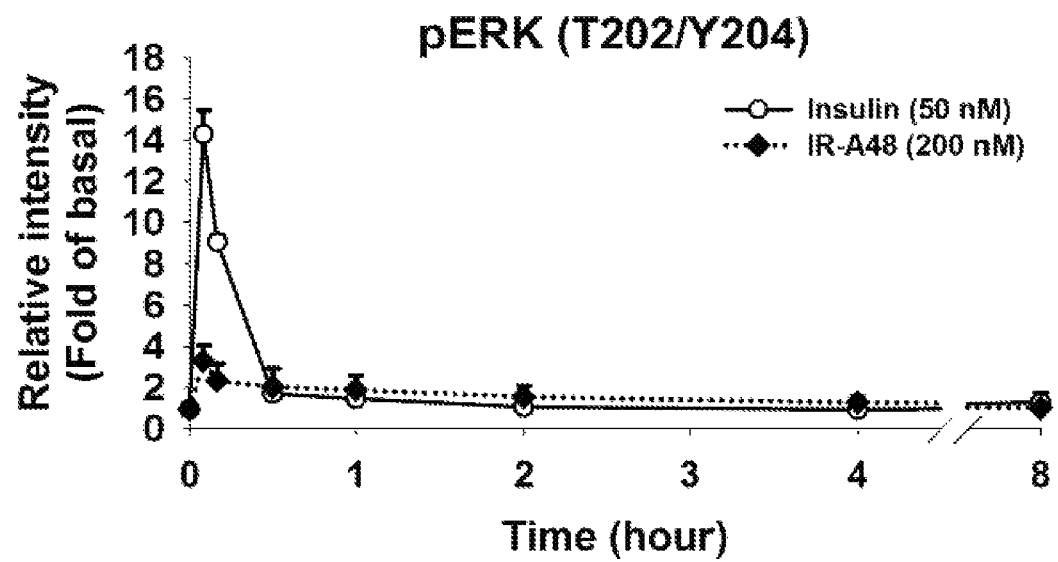

[FIG. 5a]
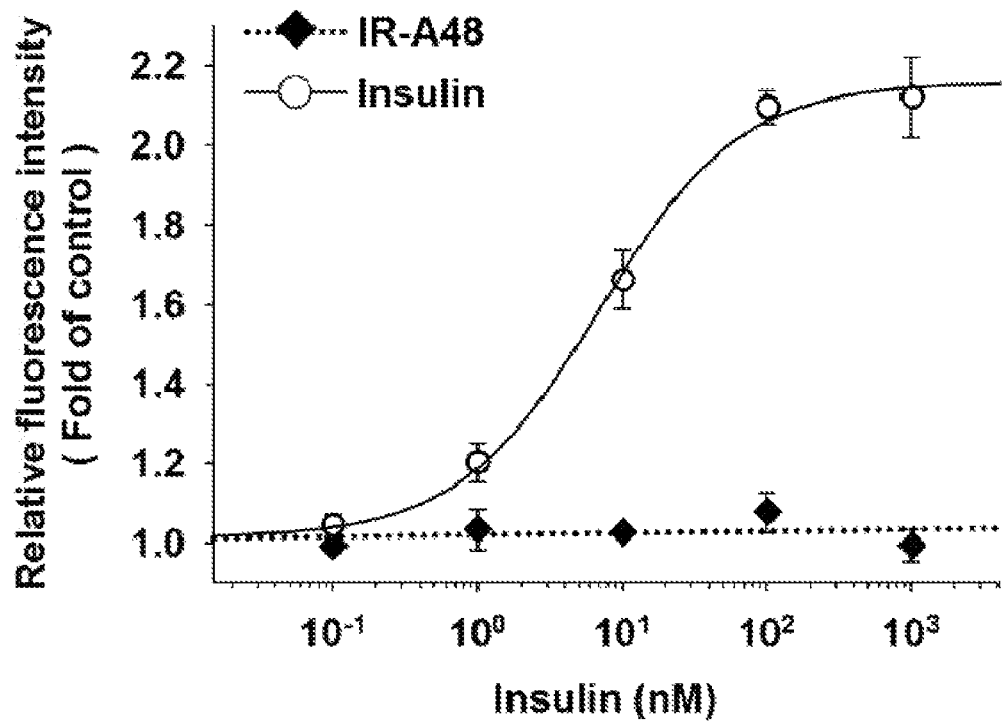

[FIG. 5b]
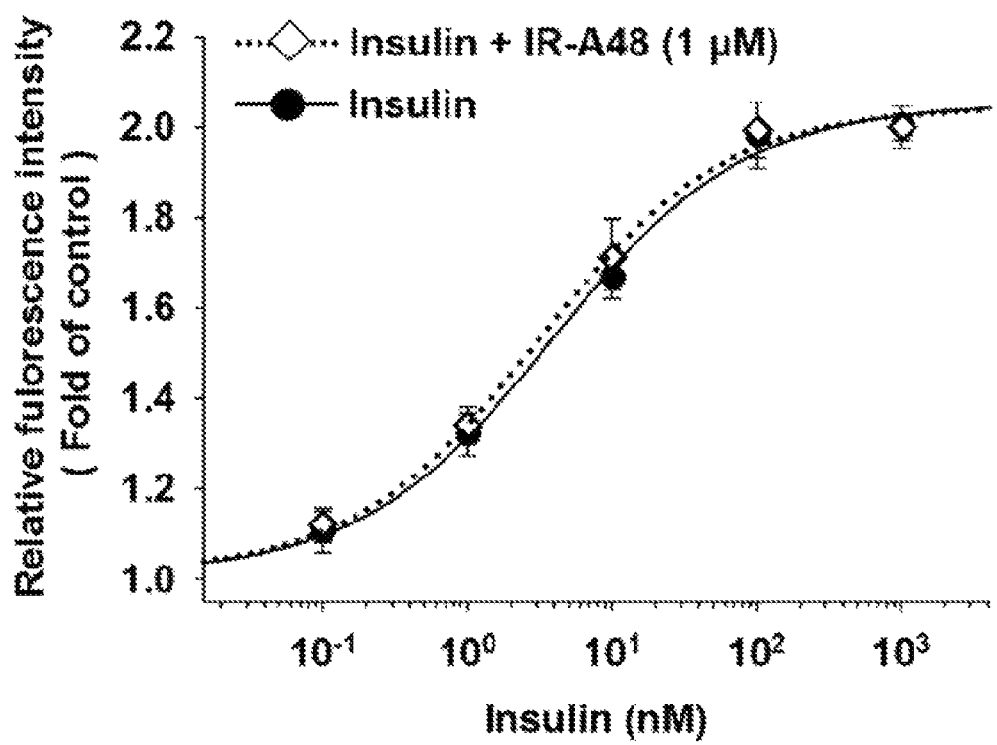

[FIG. 5c]
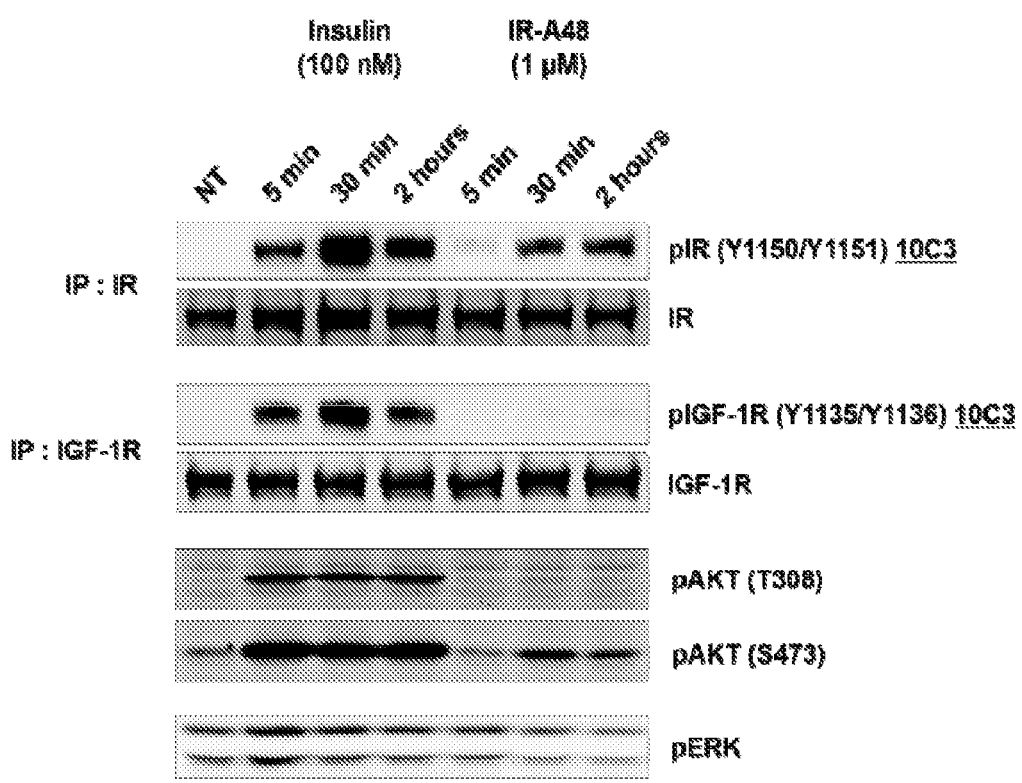

[FIG. 6a]
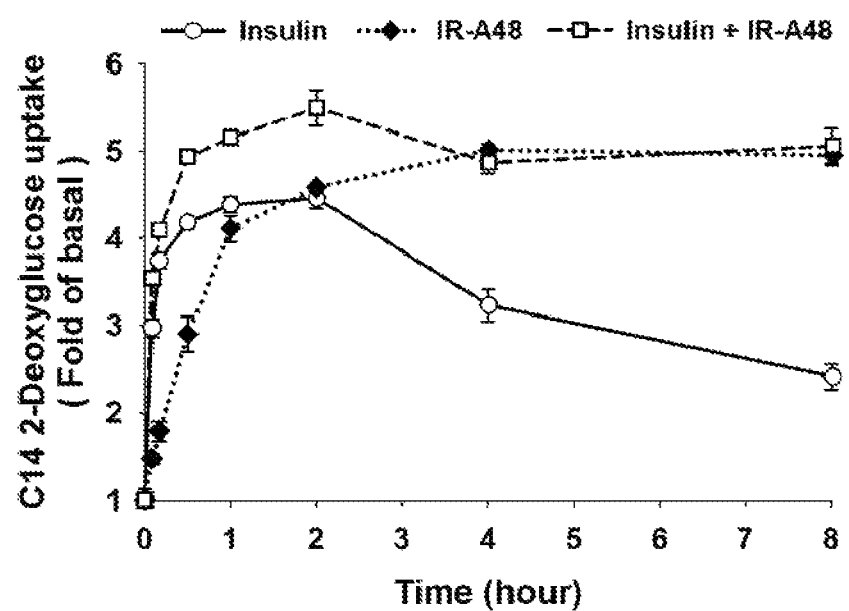

[FIG. 6b]
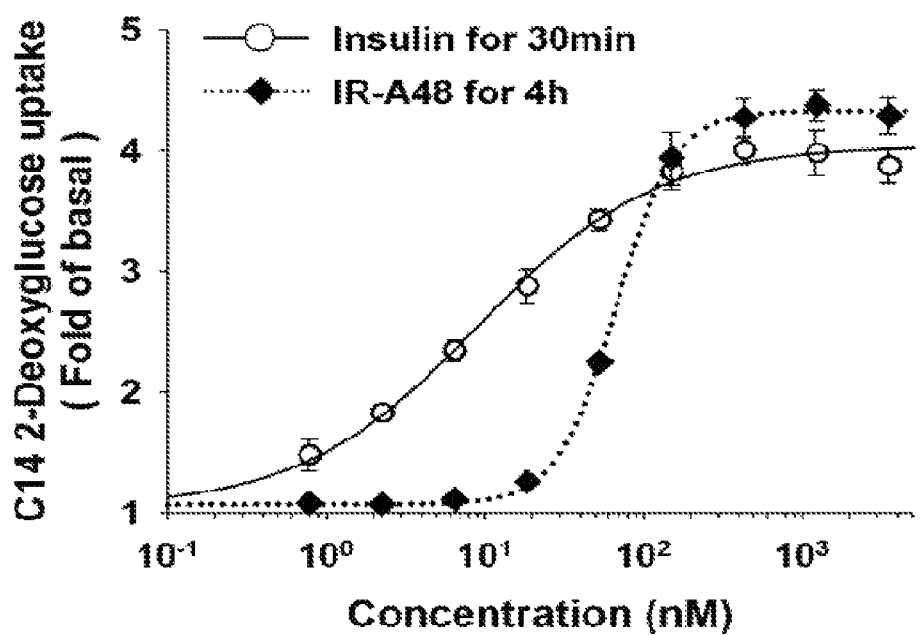

[FIG. 6c]
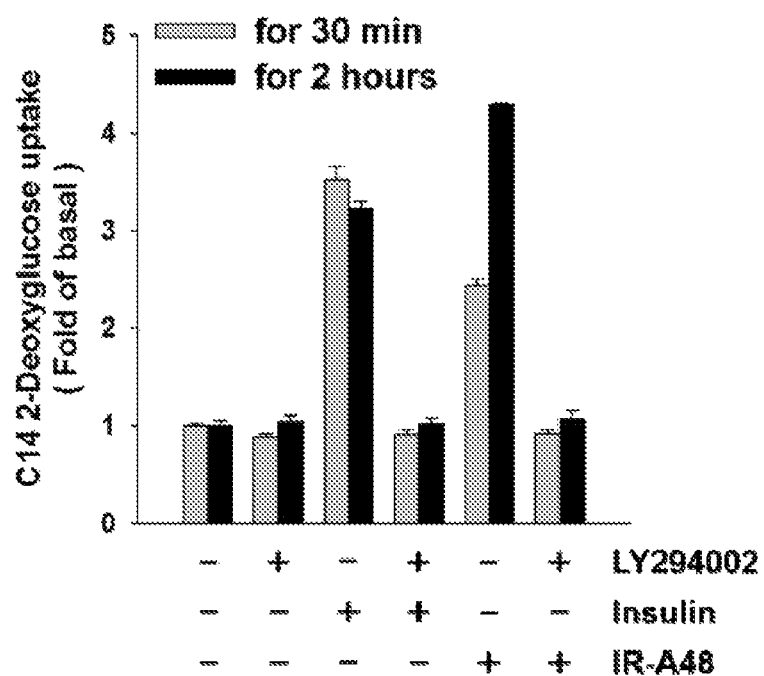

[FIG. 6d]
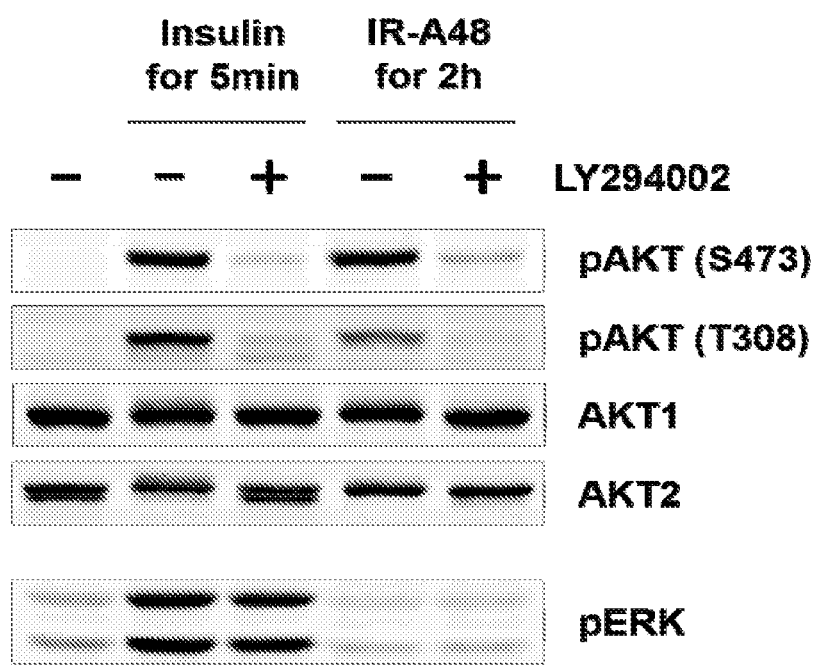

[FIG. 7]
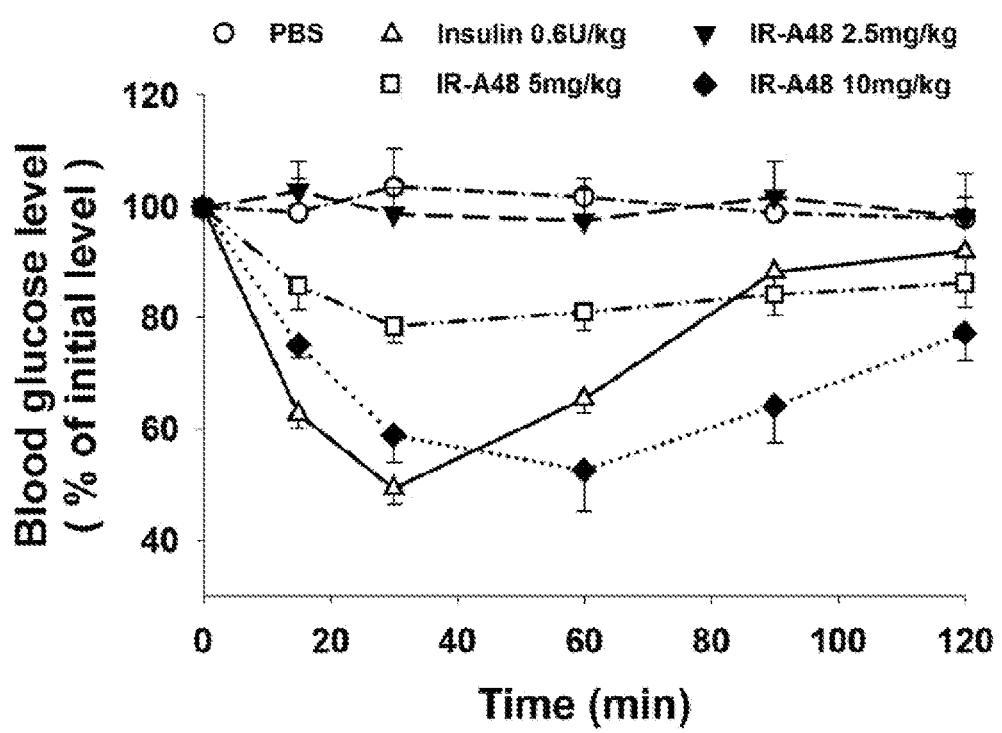

APTAMER AGAINST INSULIN RECEPTOR AND PHARMACEUTICAL COMPOSTION CONTAINING THE SAME

CROSS REFERENCE

This patent application is the U.S. National Phase under 35 U.S.C. § 371 of International Application No. PCT/KR2016/0004665, filed on May 3, 2016, which claims the benefit of Korean Patent Application No. 10-2015-0106151, filed on Jul. 27, 2015, the entire contents of each are hereby incorporated by reference.

SEQUENCE LISTING

The instant application contains a Sequence Listing which has been submitted electronically in ASCII format and is hereby incorporated by reference in its entirety. Said ASCII copy is the same as the sequence listing forming part of International Patent Application No. PCT/JP2016/004665, from which the above-identified application is a national stage commencement.

TECHNICAL FIELD

The present disclosure relates to an aptamer specifically binding to an insulin receptor and an insulin agonist using the sane, or a pharmaceutical composition for treating or diagnosing diseases related to the insulin receptor.

BACKGROUND ART

Insulin receptor (IR) is a tyrosine kinase receptor, and is a transmembrane receptor that is activated by insulin, IGF-1 or IGF-2. It is a tetramer structure in which 2 α chains (719 residues) comprising insulin-binding portion and 2 β chains (620 residues) comprising membrane penetrating portion are connected by S—S bond. When insulin binds to the receptor, the activity of the tyrosine kinase in the intracellular region of β chains becomes active and phosphorylation of tyrosine residues of receptor occurs. This autophosphorylation causes phosphorylation of other proteins.

Activation of the insulin receptor leads to glucose uptake, and the glucose uptake is inhibited when signaling of the insulin receptor is decreased, leading to secondary diabetes or related complications and hyperglycemia, etc.

Aptamer is a material which consists of 4 kinds of nucleic acids and shows specificity to the target protein according to the combination of the sequence, unlike an antibody consisting of a peptide. The aptamer specific to the target protein is produced in a test tube through SELEX (Systematic Evolution of Ligands by Exponential enrichment), and the process includes a process of finding the aptamer specifically binding to a purified protein in the random combination of pool of aptamer and amplifying it through PCR. A representative single-stranded DNA aptamer new drug, Pegaptanib is an anticancer drug that inhibits vascular epidermal growth factor binding to a vascular epidermal growth factor receptor, used for the vascular epidermal growth factor, and is approved by FDA for clinical use.

Currently, most efforts to identify functional aptamers are focused on the inhibiting ability of aptamer to the target. In particular, a variety of inhibitory aptamers have been developed for treatment of diseases, which interfere with the activity of the target molecule for clinical applications (e.g Macgen, AS1411). However, considering that intermolecular interactions are necessarily accompanied by structural changes, it is believed that activation of protein function will be possible, if aptamer-protein bond can induce a proper structural change of protein. Thus, theoretically, the aptamer has the potential to act as a functional agonist by mimicking specific protein-protein bond. However, the development of the agonist aptamer which activates functions of target remains a difficult problem at present.

In addition, in order to regulate blood sugar of patient normally, many kinds of insulin derivatives have been developed and used in these days, but insulin induces cell division in addition to glucose uptake, and the change of amino acid sequence introduced in some insulin derivatives increases binding to IGF-1 receptor and activation. Thus, the long-term administration of insulin for treating diabetes may increase incidence of cancer and there is a continuing concern about side effects caused by insulin such as atherosclerosis. In addition, it has been reported that there is a significant correlation between persistent administration of insulin and increased incidence of cancer through some epidemiological investigations. Therefore, the development of a biased agonist for insulin receptor which does not induce cell division and only increases glucose uptake will provide a good alternative to insulin administration.

Thus, there is a demand for development of an aptamer which specifically binds to insulin receptor and technology for treating or diagnosing diabetes using thereof.

DISCLOSURE

Technical Problem

Accordingly, one object of the present disclosure is to provide an aptamer for insulin receptor, which specifically binds to the insulin receptor and comprises deoxyribose uracil that is substituted by a hydrophobic functional group at 5'-position and is modified.

In addition, another object of the present disclosure is to provide a composition for treating diabetes comprising the aptamer for insulin receptor as an active ingredient, a method for treating diabetes comprising a step of administering a pharmaceutically effective dose of the aptamer for insulin receptor to a patient of diabetes, and a use for treating diabetes.

Furthermore, other object of the present disclosure is to provide a composition for diagnosing diabetes comprising the aptamer for insulin receptor as an active ingredient, and a use for diagnosing diabetes.

In addition, other object of the present disclosure is to provide a method of providing information to diagnosis of diabetes by using the aptamer for insulin receptor.

Technical Solution

In order to achieve aforementioned objects, the present disclosure provides an aptamer for insulin receptor, which specifically binds to an extracellular domain of the insulin receptor and promotes phosphorylation of the insulin receptor.

In the present description, the aptamer for insulin receptor means an aptamer which can bind to insulin with specific affinity. The insulin receptor may be derived from human insulin receptor protein, but not limited thereto.

The aptamer for insulin receptor may comprise a modified nucleotide in which 5'-position is substituted by a hydrophobic functional group. The aptamer consists of 25 to 90, preferably 27 to 80, more preferably 27 to 33 of bases, and specifically binding to the insulin receptor. The nucleotide used for the aptamer for insulin receptor of the present disclosure except for the modified nucleotide is selected from the group consisting of A, G, C, T and their deoxy forms of nucleotides, unless specifically mentioned.

The number of modified nucleotides of the aptamer for insulin receptor may be 5 to 15, preferably 6 to 8.

Preferably, the aptamer may be an aptamer for insulin receptor which comprises the nucleotide sequence of SEQ ID NO: 2 in the nucleotide sequence of SEQ ID NO: 1 named as IR-A48 and is 33 to 80 of nucleotides sequent to both sides, or an aptamer for insulin receptor which necessarily comprises the nucleotide sequence of SEQ ID NO: 7 in the nucleotide sequence of SEQ ID NO: 6, and further comprises 27 to 79 or 27 to 80 of nucleotides sequent to both sides of the nucleotide sequence of SEQ ID NO: 7.

More preferably, the aptamer may be an aptamer for insulin receptor which comprises the nucleotide sequence of SEQ ID NO: 2 in the nucleotide sequence of SEQ ID NO: 1 named and consists of 33 to 80 of nucleotides sequent to both sides, or an aptamer for insulin receptor which necessarily comprises the nucleotide sequence of SEQ ID NO: 7 in the nucleotide sequence of SEQ ID NO: 6, and consists of 27 to 79 or 27 to 80 of nucleotides.

The nucleotide sequence may be one that 5'-position of nucleotide of nucleotide comprised in the aptamer is substituted by a hydrophobic functional group, so as to increase binding ability and specificity of aptamer. For example, 5'-position of Thymine nucleotide of variable region is substituted by a hydrophobic functional group and comprises 8 of modified deoxyribose uracil, for example, 5-[N-(1-naphthylmethyl)carboxamide]-2'-deoxyuridine (Nap-dU) in the variable region. The hydrophobic functional group may comprise naphthyl group, benzyl group, pyrrole benzyl group or tryptophan, and more preferably, the hydrophobic functional group is naphthyl group.

Preferably, the aptamer for insulin receptor may form a stem-loop structure composed of internal nucleotides. More preferably, the stem-loop structure is one composed of 27 to 33 of nucleotides.

Specifically, the stem-loop structure composed of 33 nucleotides may be formed by No. 15 to 47 bp of the nucleotide sequence of SEQ ID NO: 1 named as IR-A48F, and the nucleotide sequence consisting of the No. 15 to 47 of nucleotides may be SEQ ID NO: 2. In addition, the stem-loop structure composed of 27 nucleotides may be formed by No. 26 to 45 of bases of the nucleotide sequence of SEQ ID NO: 6 named as IR-A62F, and the nucleotide sequence comprising additional nucleotides to both sides of the stem-loop structure composed of No. 26 to 45 of nucleotides may be SEQ ID NO: 7.

The present inventors verified that the aptamer for insulin receptor does not bind to IGF-1 (insulin-like growth factor) receptor having a very similar structure to the insulin receptor and specifically binds to the insulin receptor. Specifically, the aptamer for insulin receptor named as IR-A48 of the present disclosure can noncompetitively bind to insulin in a different position, and the dissociation constant (Kd) when binding to the insulin receptor is 1 nM to 20 nM, preferably approximately 3.5 to 6.9 nM. The aptamer for insulin receptor named as IR-A62 can increase the bond of insulin through positive cooperativity with insulin, and the dissociation constant (Kd) when binding to the insulin receptor is 0.5 nM to 40 nM, preferably approximately 2.4 to 26.9 nM.

The present inventors developed the aptamer which binds to the insulin receptor using SELEX method, and verified that the developed aptamer binds to the insulin receptor to phosphorylating the insulin receptor.

When insulin binds to a receptor, the receptor tyrosine residue is phosphorylated, and phosphorylation of insulin receptor increases glucose uptake by regulating movement of glucose transporter 4 (GLUT4) in adipocytes and muscle through signal transmission. The metabolic function by this insulin receptor is regulated mainly by IRS-AKT pathway, and in addition, PI3K plays an important role to phosphorylation of AKT in the process of insulin signal transmission. A publicly known PI3K inhibiting material, LY29400 completely prevents not only phosphorylation of AKT but also cell functions induced by AKT such as glucose uptake.

The aptamer for insulin receptor by the present disclosure promotes phosphorylation of the insulin receptor, and specifically phosphorylates Y1150 of the insulin receptor preferentially, and then promotes phosphorylation of AKT S473, to uptake glucose at a level of insulin. The present inventors verified that the phosphorylation and glucose uptake are induced through PI3K.

MAPK pathway is a representative pathway of signal transmission induced by the insulin receptor, and plays an important role in cell division, and insulin is also well known to induce cell division in some cancer cell lines. The present inventors verified that the aptamer for insulin receptor is an agonist of insulin and performs glucose uptake, but it does not affect cell division different from insulin. Thus, the aptamer for insulin receptor according to the present disclosure does not activate MAPK pathway different from insulin, and preferably does not affect insulin diseases by activation of MAPL pathway, and more preferably is usefully used for regulating blood sugar without affecting the increase of cancer incidence by the growth of cancer cell and atheriosclerosis by the growth of vascular smooth muscle cell.

In addition, the aptamer may modify at least one or more nucleotides positioned in 5' end, 3' end, middle or both ends, in order to enhance stability in serum and regulate renal clearance. The modification may be that one or more kinds selected from the group consisting of PEG (polyethylene glycol), biotin, idT (inverted deoxythymidine), LNA (Locked Nucleic Acid), 2'-methoxy nucleoside, 2'-amino nucleoside, 2'F-nucleoside, amine linker, thiol linker, and cholesterol, etc. are bound to 5' end, 3' end, middle or both ends and modified. 2'-methoxy nucleoside, 2'-amino nucleoside or 2'F-nucleoside invests nuclease resistance by binding to a nucleotide comprised in the aptamer and provide modified nucleotide.

Preferably, the aptamer may comprise a nucleotide modified for optimized in vivo administration by securing nuclease resistance, and more preferably, the modification may be 2'-OMe (methoxy) or 2'-F (fluor).

Two or more aptamers according to the present disclosure are linked, thereby being present as a dimer or multimer.

As used in the present application, the term "agonist of insulin receptor" represents a pharmaceutically acceptable preparation which selectively binds to the insulin receptor. Commonly, the insulin receptor agonist represents a new kind of therapeutic agent for diabetes developed to effectively regulate blood sugar. The insulin receptor agonist of the present disclosure has a property of only binding to the insulin receptor specifically and no side effects of cancer incidence.

Therefore, the agonist of insulin receptor can be used as a use for diagnosing or treating various diseases related to insulin.

Accordingly, another embodiment of the present disclosure relates to a pharmaceutical composition for preventing or treating diseases related to insulin comprising the aptamer as an agonist of insulin receptor. Other embodiment relates to a composition for diagnosing diseases related to insulin comprising the aptamer as an agonist of insulin receptor. The composition may further comprise insulin. The diseases related to insulin may comprise diabetes, diabetic complications, metabolic syndrome, obesity, cardiovascular disease, etc.

The pharmaceutical composition may be formulated as various oral administration forms or parenteral administration forms. For example, it may be any formulation for oral administration such as tablet, pill, hard/soft capsule, liquid, suspension, emulsifier, syrup, granules, elixirs, etc. These formulations for oral administration may comprise a pharmaceutically acceptable carrier such as a diluent, for example, lactose, dextrose, sucrose, mannitol, sorbitol, cellulose and/or glycine, or a glydent such as silica, talc, stearic acid, and its magnesium or calcium salt and/or polyethylene glycol, etc, other than the aforementioned active ingredient, according to the common composition of each formulation.

In addition, when the formulation for oral administration is a tablet, it may comprise a binding agent such as magnesium aluminum silicate, starch paste, gelatin, tragacanth, methylcellulose, sodium carboxymethylcellulose and/or polyvinylpyrrolidine, etc, and according to cases, comprises a disintegrating agent such as starch, agar, alginic acid, or its sodium salt, similar mixture and/or absorbent, colorant, flavoring agent, or sweetener, etc.

In addition, the pharmaceutical composition may be formulated as a parenteral administration form, and in this case, it is administered by a parenteral administration method such as subcutaneous injection, intravenous injection, intramuscular injection or intrathoracic injection, etc. Then, in order to formulate it as the formulation for parenteral administration, the pharmaceutical composition is prepared as a solution or suspension by mixing an active ingredient, that is a derivative of the chemical formula I or its pharmaceutically acceptable salt together with a stabilizer or buffering agent, and this solution or suspension may be prepared as a form of unit administration of ample or vial.

Furthermore, the pharmaceutical composition may be sterilized or further comprise an adjuvant such as a preservative, stabilizer, water dispersible powder, or activator of emulsification, salt for regulating osmosis and/or buffering agent, etc, and may further comprise other material useful therapeutically, and may be formulated according to common methods of mixing, granulating, or coating.

The subject for administration of the pharmaceutical composition of the present disclosure may be mammal including human, and preferably, may be rodents or human.

In another aspect, the present disclosure provides a method for providing information to diagnosis of diabetes using the aptamer for insulin receptor.

The method for providing information to diagnosis of diabetes may comprise a step of preparing an isolated biological sample;

a step of responding the aptamer for insulin receptor according to the present disclosure to the biological sample; and a step of measuring the level of binding of aptamer for insulin receptor in the biological sample, and be characterized by diagnosing diabetes, when the level of binding of aptamer for insulin receptor in the biological sample is higher than a normal sample.

The step of measuring the level of binding of aptamer for insulin receptor in the biological sample may be conducted using techniques for measurement of binding of DNA aptamer which are commonly used in the related technical field, and for example, a method of measuring fluorescent or radioactive intensity by labeling fluorescent or radioactive materials to the end of aptamer for insulin receptor, imaging to observe, etc. may be used, but not limited thereto.

Effect of the Invention

The aptamer for insulin receptor of the present disclosure can function as a biased agonist that selectively induces metabolic functions of the insulin receptor while promoting phosphorylation of the insulin receptor to increase glucose uptake. Furthermore, it is possible to regulate blood sugar through the insulin receptor without causing various diseases caused by insulin by activation of MAPK pathway such as increased incidence of cancer, etc.

BRIEF DESCRIPTION OF DRAWINGS

FIG. 1a shows the nucleotide sequence of IR-A48F and IR-A48 aptamers.

FIG. 1b is a secondary structure of aptamer predicted by Mfold program of Example 1.6 and shows that nucleotides of IR-A48 form a stem-loop structure.

FIG. 1c is the result of measuring whether IR-A48F or IR-A48 binds to the insulin receptor or IGF-1 receptor of Example 2.3.

FIG. 1d shows the nucleotide sequence of IR-A62F and IR-A62 aptamers.

FIG. 1e is a secondary structure of aptamer predicted by Mfold program of Example 1.6 and shows that nucleotides of IR-A62 form a stem-loop structure.

FIG. 1f is the result of measuring whether IR-A62F or IR-A62 binds to the insulin receptor or IGF-1 receptor of Example 2.3.

FIG. 2a shows the experimental result of Example 2.2 which measures FITC fluorescence change by treating FITC-insulin (100 nmol/L) and IR-A48 at a concentration of 0.1, 0.25 and 1 μm to Rat-1 fibroblast (Rat-1/hIR) that overexpresses the insulin receptor.

FIG. 2b shows the result of confirming phosphorylation of IRS, AKT, ERK by insulin and IR-A48 in Rat-1/hIR cell of Example 3.2.

FIG. 2c shows the experimental result of Example 2.2 which measures FITC fluorescence change by treating FITC-insulin (100 nmol/L) and IR-A62 at a concentration of 0.02, 0.1, 0.25, 0.5 and 1 μm to Rat-1 fibroblast (Rat-1/hIR) that overexpresses the insulin receptor.

FIG. 2d shows the result of confirming phosphorylation of IRS, AKT, ERK by insulin and IR-A62 in Rat-1/hIR cell of Example 3.2.

FIG. 3a shows the result of confirming phosphorylation of Y960, Y1146, Y1150, Y1151, Y1316 and Y1322 in the insulin receptor, caused by insulin, IR-A48 and IR-A62 of Example 3.3.

FIG. 3b is the result of measuring binding specificity to phosphorylation of Y1150, Y1151 and Y1150/Y1151 of 10C3 and pAb which are antibodies to the insulin receptor of Example 3.3.

FIG. 3c is the result of observing phosphorylation of IGF-1 receptor in HeLa cell.

FIG. 4a shows the result of confirming phosphorylation of insulin receptor protein in 3T3-L1 adipocyte in which insulin (50 nmol/L) is treated of Example 3.4.

FIG. 4b to FIG. 4d are results of Example 3.4 experiment which quantifies phosphorylation of AKT (S473), AKT (T308) and ERK (T202/Y204), respectively, caused by insulin and IR-A48.

FIG. 5a is the result of confirming the effect which affects cell growth by treating insulin and IR-A48 to MCF-7 cell, respectively, of Example 5, and FIG. 5b is the result of confirming the effect which affects cell growth by treating insulin and the mixture of insulin and IR-A48 to MCF-7 cell, and FIG. 5c is the result of confirming whether insulin and IR-A48 phosphorylates Y1150 and AKT S473 of the insulin receptor in MCF-7 cell.

FIG. 6a is a graph showing glucose uptake according to time by treating insulin, IR-A48, and the mixture of insulin and IR-A48 to 3T3-L1 adipocyte of Example 4.1.

FIG. 6b is the result of Example 4.1 observing glucose uptake after treatment for 30 min and 4 hrs, respectively, in order to measure activity according to concentration of insulin and IR-A48.

FIG. 6c is the result of comparing and investigating the increase of glucose uptake caused by IR-A48 (treatment for 2 hrs) and insulin (treatment for 30 min), after pre-treating PI3K inhibitor (LY294002) for 1 hr in 3T3-L1, in order to confirm that the activity of IR-A48 is transferred through PI3K of Example 4.2, and FIG. 6d is the result of comparing and investigating AKT phosphorylation caused by IR-A48 (treatment for 2 hrs) and insulin (treatment for 30 min), after pre-treating PI3K inhibitor (LY294002) for 1 hr in 3T3-L1, in order to confirm that the activity of IR-A48 is transferred through PI3K.

FIG. 7 is the result of observing blood sugar change for 120 min, after administering 0.6 U/kg of insulin and 2.5, 5, 10 mg/kg of IR-A48 to mice of Example 6.

DETAILED DESCRIPTION OF THE EMBODIMENTS

Hereinafter, the configuration and effect of the present disclosure will be described in detail with examples. However, the following examples are provided only for illustrative purposes in order to help understanding to the present disclosure, and the scope and range of the present disclosure are not limited thereby.

Preparation of Antibodies and Reagents

Human insulin receptor protein was purchased from R&D system (Minneapolis, Minn.) and used. The used aptamer was synthesized by Aptamer Science, Inc. (Pohang, Korea) and ST Pharm (Siheung, Korea). The antibodies used for western blotting were as follows: Anti-phosphor-ERK (T202/Y204), Anti-AKT, Anti-phosphor-AKT (S473), Anti-phosphor-AKT (T308), anti-phospho-FoxO1/3a (T24/T32), and anti-phospho-AS160 (T642) (signaling, Beverly, Mass.). Anti-IR β-subunit (C-19), anti-IGF-1R β-subunit (C-20), anti-phospho-IR (10C3, Y1150/Y1151), anti-phospho-IRS1 (Y632), and anti-phospho-Shc (Y239Y/240) antibodies were purchased from Santa Cruz Biotechnology (Santa Cruz Biotechnology, Santa Cruz, Calif.). Anti-phospho-tyrosine (4G10), anti-phospho-IRS1 (Y612) human/(Y608) mouse, and anti-phospho-IR (Y1146) (Millipore, Darmstadt, Germany). Anti-phospho-IR (Y960), anti-phospho-IR (pAb, Y1150/Y1151), anti-phospho-IR (Y1316), anti-phospho-IR (Y1322), anti-phospho-IR (Y1146/Y1150Y/1151) (Invitrogen, Carlsbad, Calif.).

Cell Culturing and Differentiation

MCF7 human breast cancer cell line, human embryonic renal cell HEK293, and mouse adipocyte 3T3-L1 were purchased from American Type Culture Collection (Manassas, Va., USA). Rat-1 fibrocyte (Rat-1/hIR) in which the insulin receptor was overexpressed was provided by Dr. Nicholas J. G. Webster of University of California. MCF7, HEK293, and Rat-1/hIR were cultured under 37° C. and 5% $CO_2$ conditions in Dulbecco's modified Eagle's medium (Lonza) in which 10% fetal bovine serum (Gibco), penicillin (100 units/ml), and streptomycin (100 units/ml) were supplemented. 3T3-L1 was cultured under 37° C. and 5% $CO_2$ conditions in Dulbecco's modified Eagle's medium (Lonza) in which 0% Bovine serum (Gibco), penicillin (100 units/ml), and streptomycin (100 units/ml) were supplemented.

After further culturing the cell grown as saturated for differentiation of adipocyte of 3T3-L1, DMEM containing 1 μM dexamethasone, 500 nM IBMX, 850 nM insulin and 10% FBS was treated for 2 days. Then, DMEM containing 850 nM insulin and 10% FBS was treated for 2 days and DMEM containing only 10% FBS was treated for 5~6 days until differentiation to adipoxyte was completed.

Example 1: Excavation of Aptamer for Insulin Receptor

The aptamers which bind to an extracellular domain of the insulin receptor were excavated using SELEX. SELEX was progressed using single-stranded DNA library consisting of 40mer of variable nucleotide sequence and constant nucleotide sequences which are present in both sides each as 20mer (SEQ ID NO: 3).

1.1 Synthesis of Modified Nucleic Acid Library

In order to prepare a single chain modified DNA library needed for SELEX, an antisense library in which biotin bound to 5' (SEQ ID NO: 3) was synthesized. The antisense library responded with a 50 uM of reverse primer (SEQ ID NO: 4) at 70° C. for 1 hr on 0.5 mM of dNTP (ATP, GTP, CTP, Bz-dU), 0.25 U/ul of KOD XL (Invitrogen), 10× extension buffer (1.2M Tris-HCl pH7.8, 100 mM KCl, 60 mM (NH4)2SO4, 70 mM MgSO4, 1% TritonX-100, 1 mg/mlBSA) to prepare a double helix DNA. The single chain modified DNA library was eluted using 20 mM NaOH thereto, and then neutralized with HCL solution. The prepared DNA library was concentrated using Amicon ultra-15 (Millipore), and then quantified with a spectrophotometer.

1.2. Bond with Insulin Receptor

After putting 1 nmole of the synthesized library into a selection buffer (200 mM HEPES, 510 mM NaCl, 25 mM KCl, 25 mM MgCl2) and reacting it at 95° C., 70° C., 48° C., 37° C. for 5 min, respectively, 10 μL of 10× protein competition buffer (10 μM prothrombin, 10 μM casein, 0.1% (w/v) HSA (human serum albumin, SIGMA) was mixed for negative selection, and then it was added to Dynabeads® MyOne™ Streptavidin C1 (SA bead) (50% (v/v) slurry, 10 mg/ml Invitrogen) in which supernatant was removed and reacted at 37° C. for 10 min.

After the response of negative selection, only supernatant was collected and moved to a new tube, and then reacted in Dynabead TALON bound to insulin receptor protein to which His tag bound at 37° C. for 1 hr. Dynabeads TALON to which DNA and insulin receptor bound was washed for 5 times with 100 μL of the selection buffer (200 mM HEPES, 510 mM NaCl, 25 mM KCl, 25 mM MgCl2). At the fifth washing, it was moved to a new plate and washed. 85 μL of 2 mM NaOH solution was added and the library which binds to the target was eluted, and then neutralized with 20 μL of 8 mM HCl solution.

1.3 Amplification

The library DNA which binds to the target was amplified using QPCR (quantitative PCR, IQ5 multicolor real time PCR detection system, Bio-rad). The above reverse primer (SEQ ID NO: 4) and antisense library (SEQ ID NO: 3) used for preparation of the library were mixed so as that the total volume of 5 uM (5×QPCR master Mix, Novagen), 0.075 U/ul KOD (Novagen), 1 mM dNTP (Roche Applied science), 25 mM MgCl2, 5×SYBRgreen I (Invitrogen) was 125 µL, respectively, thereby preparing a double-stranded library by repeating once under the condition of 96° C. 15 sec, 55° C. 10 sec, and 68° C. 30 min, and 30 times under the condition of 96° C. 15 sec, and 72° C. 1 min.

1.4. eDNA Preparation eDNA means an aptamer produced by using DNA template and polymerase as an enzymatic DNA. The DNA library prepared by the above QPCR was mixed in 25 µL Myone SA bead (Invitrogen) at a room temperature for 10 min and fixed. Then the amount of mixed DNA was 60 ul as the QPCR product. 20 mM NaOH solution was added and it was made to a single-stranded DNA. And the DNA which comprises the nucleic acid modified by the same method as the library preparation of Example 1.1 was synthesized and used next time. SELEX round was conducted for 8 times in total, and for more selective binding, from 4th time to 6th time and from 7th time to 8th time, DNA and protein (IntegrinαVβ3) complex were diluted in 10 mM DxSO4 (sigma) solution to be 1/200, 1/400, respectively, and then the aptamer was sorted.

1.5. Analysis of Aptamer Nucleotide Sequence

After passing through 8 times of SELEX rounds, its output was amplified as a double-stranded DNA by QPCR method, and then cloned using TA cloning kit (SolGent). And the nucleotide sequence of aptamer was obtained by sequencing with M13 primer which was present on the vector (SEQ ID NO: 5).

1.6. Optimum Aptamer Sequencing

The excavated aptamer (1 uM) was treated to HEK293 cell in which the insulin receptor was overexpressed to find the aptamer, to analyze whether phosphorylation of AKT S473 increased. Most of aptamers had no effect, but the excavated IR-A48F and IR-A62F aptamers increased phosphorylation of AKT significantly. The sequence of IR-A48F and IR-A62F consists of 80mer comprising 8 of Nap-dU in the variable region (FIG. 1a, FIG. 1d), and the minimization of aptamer sequence was conducted based on the secondary structure of aptamer to find the minimum sequence of aptamer needed for binding to the target.

The secondary structure of IR-A48F aptamer predicted by Mfold program was shown in FIG. 1b, and 33 of nucleotides in the aptamer including 6 of Nap-dU formed a stable stem-loop structure. The secondary structure of IR-A62F aptamer predicted by Mfold program was shown in FIG. 1e, and 27 of nucleotides in the aptamer including 6 of Nap-dU formed a stable stem-loop structure.

As the result of the above experiment, it was verified that this internal stem-loop sequence (IR-A48) (3.5 nM Kd) bound to the insulin receptor at a similar level to IR-A48F (6.9 nM Kd) by analysis of binding to the target. In addition, it was verified that IR-A48 had very high specificity to the insulin receptor, as it did not bind to the insulin-like growth factor 1 (IGF-1) receptor which had a very similar structure to the insulin receptor. Similarly, as the result of investigating the effect of IR-A48 to phosphorylation of IGF-1 receptor using 10C3 antibody, IR-A48 did not affect phosphorylation of IGF-1 receptor at all, different from insulin. The result was shown in FIG. 1c and FIG. 3c.

In addition, it was verified that the internal stem-loop sequence (IR-A62) (2.4 nM Kd) bound to the insulin receptor at a similar level to IR-A48F (26.9 nM Kd) by analysis of binding to the target. In addition, it was verified that IR-A62 had very high specificity to the insulin receptor, as it did not bind to the insulin-like growth factor 1 (IGF-1) receptor which had a very similar structure to the insulin receptor. Similarly, as the result of investigating the effect of IR-A62 to phosphorylation of IGF-1 receptor using 10C3 antibody, IR-A48 did not affect phosphorylation of IGF-1 receptor at all, different from insulin. The result was shown in FIG. 1f and FIG. 3c.

All the following experiments were conducted by using IR-A48 and IR-A62 in which minimization was progressed.

1.7. Synthesis and Purification of Aptamer

The aptamer was synthesized by us by Solid Phase Oligo Synthesis method using Mermade 12 synthesizer from Bio-automation Company, which is a nucleic acid-only fixed synthesizer. It was synthesized with solide phase b-cyanoethyl phosphoramidite chemistry using an oligonucleotide synthesizer (Bioautomation, Mermade12), and after synthesis, CPG (200 nmole synthesis column, 1000A (MM1-1000-)) was put in a cleavage solution [t-butylamine:methanol:water (1:1:2 volume ratio)] and vacuum dried, and then it was isolated/purified by using HPLC (GE, AKTA basic). The used column was RP-C18 column (Waters, Xbridge OST C18 10×50 mm), and 0.1M TEAB/Acetonitrile Buffer was used under the condition of UV 254 nm/290 nm, flow rate: 5 ml/min, temperature: 65° C. For these aptamers, their accurate molecular weights were measured in 0.02% error range with LC-ESI MS spectrometer (Waters HPLC systems (Waters)+Qtrap2000 (ABI)) all and 80-90% was obtained in purity measurement using HPLC.

Example 2: Binding Properties of Aptamer for Insulin Receptor

2.1. Preparation for Cell Experiment

Before treating the aptamer, cells were treated in DMEM with no FBS for 3 hrs for serum deficiency. Then for 1 hr, cells were treated in Krebs-Ringer HEPES buffer [25 mM HEPES (pH 7.4), 120 mM NaCl, 5 mM KCl, 1.2 mM MgSO4, 1.3 mM CaCl2), and 1.3 mM KH2PO4]. All the aptamers for cell treatment were prepared in the equivalent Krebs-Ringer HEPES buffer, and passed through a process of heating at 95° C. for 5 min and cooling at a room temperature slowly for the formation of accurate secondary structure.

2.2. Insulin Competition Assay

In order to investigate binding properties to the insulin receptor of the excavated IR-A48 and IR-A62 in Example 1, insulin competition assay was progressed using a flow cytometry. Rat-1/hIR cell was removed from a cell culture container using PBS containing 5 mM EDTA. A blocking buffer (PBS, 1% BSA, and 0.1% NaN3) was treated to the prepared cell and reacted at 4° C. for 30 min at 20 rpm. Then the insulin to which FITC bound was treated with various concentrations of IR-A48 and reacted at 4° C. for 1 hr so as that each binding becomes equilibrium. After washing the cell twice with PBS, it was fixed at a room temperature for 30 min with PBS containing 4% paraformaldehyde. The amount of insulin which bound to the cell was observed by measuring fluorescence of FITC by a flow cytometry (BD FACSCanto™ II).

As a result, it was verified that IR-A49 did not interfere with binding of insulin, although it had the activity as an agonist (FIG. 2a). This means that IR-A48 binds to a completely different allosteric site, not an orthosteric site where insulin binds. It was verified that IR-A62 had a positive cooperativity which increases binding of insulin, although it had the activity as an agonist (FIG. 2c).

2.3. Filter Binding Assay

In order to investigate binding capacity of the selected aptamer, filter binding assay was conducted. At first, α-P32ATP (PerkinElmer) was labeled with TdT (Terminal deoxynucleotidyl transferase, NEB) at 5' end of the aptamer. The aptamer 1 μM 0.25 μL, α-P32ATP (5 μM, perkinelmer), 0.25 μL, TdT and 10×NEB buffer4 10 μL reaction volume were reacted at 37° C. for 30 min, and incubated at 70° C. for 10 min, to inactivate TdT. The labeled DNA pool was purified by using Micro spin G-50 column (GE healthcare).

The labeled aptamer 20,000 cpm was put in 100 μL 1×SB buffer (200 mM HEPES, 510 mM NaCl, 25 mM KCl, 25 mM MgCl2) and cooled slowly by 37° C. as 0.1° C. per 1 sec from 95° C. And, after the insulin receptor protein was diluted in order as 102 point at 100 nM by using buffer (200 mM HEPES, 510 mM NaCl, 25 mM KCl, 25 mM MgCl$_2$), the heated and cooled DNA pool 30 μL was added respectively and reacted at 37° C. for 30 min. After spotting the mixture of DNA and IntegrinαVβ3 as 2 μL, respectively to Nylon membrane (GE healthcare), zorbax resin (Agilent) 5.5 μL was added. And it was put into Durapore filter (Millipore) wet with 1×SB buffer (200 mM HEPES, 510 mM NaCl, 25 mM KCl, 25 mM MgCl2) 50 μL in advance and vacuumed. Then the membrane filter was washed with 100 μL of 1× selection buffer (200 mM HEPES, 510 mM NaCl, 25 mM KCl, 25 mM MgCl2). After exposing the filter plate to an image plate overnight, the image was quantified with FLA-5100 (Fuji).

As a result, it was verified that Kds of IR-A48 and IRA48F were 3.5 nM and 6.9 nM, respectively, and IR-A48 bound to the insulin receptor, but did not bind to IFG-1 receptor. The result was shown in FIG. 1c.

In addition, it was verified that Kds of IR-A62 and IR-A62F were 2.4 nM and 26.9 nM, respectively, and IR-A62 bound to the insulin receptor, but did not bind to IFG-1 receptor. The result was shown in FIG. 1f.

Example 3: Phosphorylation of Aptamer for Insulin Receptor 3.1. Western Blot

In order to observe phosphorylation of the insulin receptor and signal transmission protein, cells were dissolved in a dissolution buffer [50 mM Tris-HCl (pH 7.4), 150 mM NaCl, 1 mM EDTA, 20 mM NaF, 10 mM β-glycerophosphate, 2 mM Na3VO4, 1 mM PMSF, 10% glycerol, 1% Triton-X, and protease inhibitor cocktails]. The lysates were centrifuged at 95° C. for 15 min at 14,000 rpm, to isolate the protein. The prepared lysates were under electrophoresis on 6%~16% SDS-PAGE and moved to a nitrocellulose membrane. After reacting the primary antibody to the membrane at 4° C. for 12 hrs, the secondary antibody to which HPR (Horseradish peroxidase) or IRDye800CW (LI-COR) bound was reacted at a room temperature for 1 hr. The presence of protein and level of phosphorylation was measured by using Chemiluminescence by ECL (Thermo Scientific, MA) or Infrared fluorescence system (Odyssey, LI-COR).

3.2. Phosphorylation of Insulin Receptor

In order to investigate the effect of IR-A48 and IR-A62 aptamers of Example 1 on binding of insulin, the level of phosphorylation of insulin receptor was observed by the aforementioned western blotting in case of treating IR-A48, IR-A62, and insulin, and the result was shown in FIG. 2b and FIG. 2d.

The phosphorylation of IRS, AKT and ERK caused by insulin in Rat-1/hIR cell was not affected, although IR-A48 or IA-A62 was treated together. However, the phosphorylation of insulin receptor caused by IR-A48 or IR-A62 was different from insulin. The phosphorylation of Y1150/Y1151 of the insulin receptor kinase region increased by both insulin and IR-A48 or IR-A62. When Ir-A48 was treated with insulin, the phosphorylation of Y1150/Y1151 increased cooperatively, and when IR-A48 was treated with insulin, the phosphorylation of Y1150/Y1151 was greatly amplified. The total tyrosine phosphorylation greatly increased only by insulin, and the effect of IR-A48 and IR-A62 was insignificant. Taken together, these results exhibited that IR-A48 functioned independently of insulin, and IR-A62 amplified the activity of insulin, but the activity was weighted towards to specific tyrosine (Y1150/Y1151) in the kinase region.

3.3. ELISA-Intracellular Tyrosine Phosphorylation

In order to investigate the effect of phosphorylation of IR-A48 and IR-A62 aptamers excavated in Example 1, 6 kinds of antibodies were used. When insulin binds to the receptor, 7 of tyrosines (Y953, Y960, Y1146, Y1150, Y1151, Y1316 and Y1322) is phosphorylated, but an antibody against Y953 among them was not developed, and thus 6 kinds of tyrosines in total were experimented.

ELISA was conducted to observe antigen specificity of antibody, and at first, 3 kinds of peptides (MTRDIYETD-pY-pY-RKGGKGLL, MTRDIYETD-pY-YRKGGKGLL, MTRDIYETDY-pY-RKGGKGLL) used as antigens were synthesized in Selleckchem (Houston, Tex.). 20 pmol/100 μl of peptide melted in PBS was reacted at 4° C. for 12 hrs in a 96 plate (Corning, Mass.) coated with N-oxysuccinimide ester groups and linked by the covalent bond. After blocking for 1 hr with PBS containing 1% BSA, it was washed with TTBS buffer [50 mM Tris-HCl (pH 7.6), 150 mM NaCl, and 0.05% Tween-20] once. After diluting antibodies in TTBS buffer as 1:1000, it was bound to the antigen which bound to the 96 plate. After washing with TTBS buffer 3 times, it was diluted with the secondary antibody to which AP (Alkaline phosphatase) bound as 1:2000, and bound at a room temperature for 1 hr. After washing with TTBS buffer 3 times, 100 ul of CSPD was added and reacted at a room temperature for 30 min, and then chemical luminescence was measured by using a photometer (Luminoskan Ascent).

In order to clearly demonstrate phosphorylation biased to Y1150/Y1151, 2 different kinds of pY1150/pY1151 antibodies were used: 10C3 (sc-81500, Santa Cruz) pAb (44804G, Invitrogen). In addition, since Y1150 and Y1151 were phosphorylated independently, it was assumed that two antibodies had specificity to pY1150, pY1151, pY1150/pY1151, different each other, respectively, and in order to demonstrate that, specificity of antibody was verified through ELISA as preparing synthesized peptides corresponded to pY1150, pY1151, pY1150/pY1151.

The result was shown in FIG. 3a, and it was shown that insulin increased all phosphorylation of Y960, Y1146, Y1150, Y1151, Y1316, Y1322, but IR-A48 and IR-A62 increased phosphorylation of Y1150/Y1151 of the kinase region only.

As can be seen FIG. 3b, 10C3 antibody bound to pY1150/pY1151 and pY1150 all at a similar level, but pAb antibody strongly bound to pY1150/pY1151 only. It was demonstrated that IR-A48 is a biased agonist which phosphorylates Y1150 of the insulin receptor kinase region only preferentially by the result.

3.4. Phosphorylation of Signal Transmission Protein

The effect of Y1150 phosphorylation caused by IR-A48 excavated in Example 1 on insulin signal transmission was compared with insulin.

As the result of the above experiment, IR-A48 activated signal transmission comparable to insulin. The phosphorylation of insulin receptor and protein such as IRS, AKT, ERK, etc in 3t3-L1 adipocyte where insulin (50 nmol/L) was treated increased rapidly for 5 min, and as time went by, decreased gradually. IR-A48 (200 nmol/L) increased phosphorylation of RS (Y608, Y632), AKT (T308, S473), AS160 (T642), GSK3 α/β (S21/S9), FOXO1/3a (T24/T32) slowly for 2 hrs and the phosphorylation continued for 4 hrs, by contrast with insulin. The above result was shown in FIG. 4a.

The phosphorylation of insulin receptor plays two roles in signal transmission, and at first, the phosphorylation of kinase region (Y1146, Y1150, Y1151) regulates the activity of kinase, and second, the phosphorylation of Y960 and Y1322 is used for the binding position of signal transmission protein which binds to the insulin receptor. Considering this phosphorylation biased to Y1150, it was verified that IR-A48 exhibited unexpected effect by showing the activity of signal transmission at the level of insulin, although IR-A48 was regarded as not greatly increasing insulin signal transmission due to low phosphorylation of other tyrosines.

Above all, IR-A48 exhibited the activity biased to specific biased insulin signal transmission. About 98% of high level of phosphorylation was shown by IR-A48 compared with insulin of AKT S483, but the phosphorylation of AKR T308 remained only 37% (FIGS. 4A, 4B and 4C). In addition, IR-A48 hardly affected the phosphorylation of EKR (FIGS. 4A and 4D). As such, IR-A48 activated signal transmission of insulin receptor, but had completely different properties from signal transmission by insulin.

Example 4: Glucose Uptake of Aptamer for Insulin Receptor 4.1 Glucose Uptake in 3T3-L1 Adipocyte Since IR-A48 excavated in Example 1 increased the phosphorylation of AKT S473, the activity of IR-A48 to glucose uptake was investigated in 3T3-L1 adipocyte.

For serum deficiency, the completely differentiated 3T3-L1 adipocyte was treated in DMEM with no FBS for 3 hrs, and then it was treated with Krebs-Ringer HEPES buffer for 1 hr. After treating insulin or aptamer for relevant hours, 2-deoxy[14C]glucose (0.1 µCi/ml) was treated for 10 min. It was washed with PBS in which 20 mM glucose was added 3 times, and the cell was melted with a solution containing 0.5 N NaOH and 1% SDS. The amount of 2-Deoxy-D-glucose absorbed in the cell was observed by using a liquid scintillation counter.

When insulin (50 nmol/L) was treated to 3T3-L1 adipocyte, the glucose uptake increased the highest from 30 min to 1 hr, but decreased slowly and after 8 hrs, decreased below the half. Despite of the phosphorylation biased to Y1150, IR-A48 (200 nmol/L) increased the glucose uptake at a similar level to insulin. However, similar to phosphorylation pattern of signal transmission protein, the glucose uptake also increased slowly by 4 hrs, and maintained over 8 hrs. In addition, when IR-A48 and insulin were treated together, the glucose uptake increased cooperatively due to the allosteric binding of IR-A48. The result was shown in FIG. 6a.

Despite of slow increase speed, IR-A48 increased sufficiently at the high concentration. In order to measure the activity of insulin and IR-A48 according to the concentration, the glucose uptake at the time of treatment when the highest response was shown, respectively was observed (insulin was 30 min, IR-A48 was 4 hrs). At the highest concentration, both insulin and Ir-A48 exhibited the similar level of saturated glucose uptake. However, insulin exhibited slowly increased glucose uptake according to the concentration (Hill coefficient: 0.77), but IR-A48 exhibited rapidly increased form between 20 nmol/L and 200 nmol/L (Hill coefficient: 0.77). As a result, EC50 of IR-A48 (66.2 nmol/L) was higher than insulin (8.9 nmol/L), but EC95 of IR-A48 (202.4 nmol/L) was slightly lower than insulin (261.9 nmol/L). The result was shown in FIG. 6b.

4.2 Inducement of Glucose Uptake by PI3K

In order to verify whether the activity of IR-A48 excavated in Example 1 was transferred through PI3K, the increase of AKT phosphorylation and glucose uptake by IR-A48 was investigated, after treating PI3K inhibitor (LY294002) in 3T3-L1 for 1 hr. As a result, it was verified that not only glucose uptake by IR-A48 but also phosphorylation of AKT were inhibited by LY294002. The result was shown in FIG. 6c and FIG. 6d, and this exhibited that the increase of AKT phosphorylation and glucose uptake by IR-A48 was induced by PI3K as same as insulin.

Example 5: Inducement of Cancer Cell Growth

In order to investigate the effect on cell division of IR-A48 excavated in Example 1, MCF-7 cancer cell line which was widely used to experiment the ability of inducement of cell division of insulin was used.

After culturing MCF7 cell in a 24-well plate as 10000 cells per well, it was grown for 24 hrs. For serum deficiency, it was additionally grown with 0.5% FBS DMEM for 24 hrs. Insulin or aptamer was treated for 72 hrs, and the medium was newly replaced whenever 24 hrs went. After finishing treatment, the cell was fixed at a room temperature for 30 min with PBS containing 4% paraformaldehyde. DNA which the cell had was dyed with PBS containing 1 µM SYTO60 fluorescent pigment, and then fluorescence was measured with LI-COR Odyssey scanner, thereby quantifying the amount of cell.

As the result of treating insulin and IR-A48 to MCF-7 separately respectively, insulin increased cell division at 2.1 fold, but IR-A48 did not affect it at all. In addition, when IR-A48 (1 umol/L) was mixed and treated with insulin, it also did not affect the cell division by insulin at all. In order to exclude possibility in that IR-A48 did not activate the insulin receptor which was present in MCF-7 cell, the insulin signal transmission by IR-A48 in MCF-7 cell was verified. As a result, it was verified that it phosphorylated the insulin receptor Y1150 and AKT S473 in MCF-7 cell as same as 3T3-L1 adipocyte. The result was shown in FIG. 5a to FIG. 5c, and as a result, it was shown that the signal transmission induced by IR-A48 had a completely separated function with inducement of cell division by the insulin receptor.

Example 6: In Vivo Blood Sugar Experiment

In order to demonstrate the results of Example 3 to Example 6 in vivo, the effect on blood sugar of mice of IR-A48 excavated in Example 1 was measured.

To prevent that IR-A48 was rapidly degraded by 3' exonuclease in blood, inverted deoxythymidine (idT) was added to 3' end of IR-A48. After fasting 8-week age of male C57Bl/6J experimental mice for 12 hrs, 10 mg/kg, 5 mg/kg, 2.5 mg/kg of IR-A48 was melted in PBS and administered by intravenous injection to the experimental mice. When 15 min, 30 min, 60 min, 90 min and 12 min passed after administration, the change of blood sugar was observed with a blood sugar monitoring device (Accu-Check Active; Roche Diagnostics) by collecting blood from their tails. In 30 min after administration, the blood sugar of the mouse in which 10 mg/kg IR-A48 was administered (41% reduction) was decreased at a similar level to 0.6 unit/kg of insulin (51% reduction). However, different from insulin in which blood sugar was rapidly recovered in 30 min, for the mice in which IR-A48 was administered, the blood sugar exhibited the pattern of being persistently decreased by 1 hr, and after that, slowly recovered. The result was shown in FIG. 7.

It was verified that IR-A48 had the activity not only in vitro but also in vivo through this, and this exhibited that IR-A48 could regulate blood sugar independently of insulin through allosteric regulation.

The invention claimed is:

1. An aptamer for insulin receptor, which specifically binds to an extracellular domain of the insulin receptor and promotes phosphorylation of the insulin receptor, wherein the aptamer comprises the nucleotide sequence of SEQ ID NO: 2 or SEQ ID NO: 7.

2. The aptamer for insulin receptor of claim 1, wherein the aptamer comprises the nucleotide sequence of SEQ ID NO: 2.

3. The aptamer for insulin receptor of claim 1, wherein the aptamer essentially consists of the nucleotide sequence of SEQ ID NO: 1, or consists of 33 to 80 consecutive nucleotides connected to at least one end of the nucleotide sequence of SEQ ID NO: 2.

4. The aptamer for insulin receptor of claim 1, wherein the aptamer essentially consists of the nucleotide sequence of SEQ ID NO: 6, or consists of 27 to 80 consecutive nucleotides connected to at least one end of the nucleotide sequence of SEQ ID NO: 7.

5. The aptamer for insulin receptor of claim 1, wherein the aptamer comprises the nucleoride sequence of SEQ ID NO: 7.

6. The aptamer for insulin recepter of claim 1, wherein at least one nucleotide comprised in the aptamer is modified by connecting with one or more kinds selected from the group consisting of PEG (polyethlene glycol), biotin, idT (inverted deoxythymidine), LNA (Locked Nucleic Acid), 2'-methoxy nucleoside, 2'-amino nucleoside, 2'F-nucleoside, amine linker, thiol linker, and cholesterol.

7. The aptamer for insulin recepter of claim 1, which is dimer or multimer.

8. An insulin receptor agonist, comprising the aptamer for incsulin recepter of claim 1.

9. A pharmaceutical composition for preventing or treating insulin-related disease, comprising the aptamer for insulin receptor according to claim 1 as an active ingredient.

10. The pharmaceutical composition of claim 9, further comprising insulin.

* * * * *

SEQUENCE LISTING

```
<160> NUMBER OF SEQ ID NOS: 7

<210> SEQ ID NO 1
<211> LENGTH: 80
<212> TYPE: DNA
<213> ORGANISM: Artificial Sequence
<220> FEATURE:
<223> OTHER INFORMATION: IR-A48F
<220> FEATURE:
<221> NAME/KEY: misc_feature
<222> LOCATION: (22)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (24)..(25)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (35)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (37)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (41)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (51)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (58)
<223> OTHER INFORMATION: 2-deoxyuridine which is modifed by hydrophobic
      group selected from the group consisting of benzyl, naphtyl,
      pyrrolbenzyl and tryptophanyl

<400> SEQUENCE: 1
tatgagtgac cgtccgcctg gngnnaagac aaccncnagg ncaggcgcag ngacgggnag      60
cagccacacc accagccaaa                                                  80

<210> SEQ ID NO 2
<211> LENGTH: 33
<212> TYPE: DNA
<213> ORGANISM: Artificial Sequence
<220> FEATURE:
<223> OTHER INFORMATION: IR-A48
<220> FEATURE:
<221> NAME/KEY: misc_feature
```

```
<222> LOCATION: (8)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (10)..(11)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (21)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (23)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (27)
<223> OTHER INFORMATION: 2-deoxyuridine which is modifed by hydrophobic
      group selected from the group consisting of benzyl, naphtyl,
      pyrrolbenzyl and tryptophanyl

<400> SEQUENCE: 2
cgcctggngn naagacaacc ncnaggncag gcg                                    33

<210> SEQ ID NO 3
<211> LENGTH: 80
<212> TYPE: DNA
<213> ORGANISM: Artificial Sequence
<220> FEATURE:
<223> OTHER INFORMATION: a modified single strand DNA (ssDNA) library
      with 40 mer random region
<220> FEATURE:
<221> NAME/KEY: misc_feature
<222> LOCATION: (21)..(60)
<223> OTHER INFORMATION: random region containing 2-deoxyuridine which
      is modifed by naphtyl group

<400> SEQUENCE: 3
tttggctggt ggtgtggctg nnnnnnnnnn nnnnnnnnnn nnnnnnnnnn nnnnnnnnnn        60
caggcggacg gtcactcata                                                   80

<210> SEQ ID NO 4
<211> LENGTH: 14
<212> TYPE: DNA
<213> ORGANISM: Artificial Sequence
<220> FEATURE:
<223> OTHER INFORMATION: reverse primer

<400> SEQUENCE: 4
tgaccgtccg cctg                                                         14

<210> SEQ ID NO 5
<211> LENGTH: 17
<212> TYPE: DNA
<213> ORGANISM: Artificial Sequence
<220> FEATURE:
<223> OTHER INFORMATION: M13 primer

<400> SEQUENCE: 5
caggaaacag ctatgac                                                      17

<210> SEQ ID NO 6
```

```
<211> LENGTH: 79
<212> TYPE: DNA
<213> ORGANISM: Artificial Sequence
<220> FEATURE:
<223> OTHER INFORMATION: IR-A62F
<220> FEATURE:
<221> NAME/KEY: misc_feature
<222> LOCATION: (24)..(25)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (31)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (35)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (37)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (41)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (45)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (52)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (58)..(59)
<223> OTHER INFORMATION: 2-deoxyuridine which is modifed by hydrophobic
      group selected from the group consisting of benzyl, naphtyl,
      pyrrolbenzyl and tryptophanyl

<400> SEQUENCE: 6
tatgagtgac cgtccgcctg gcannacgca ngagncnaga nccgncagac cnaaggcnnc     60
agccacacca ccagccaaa                                                  79

<210> SEQ ID NO 7
<211> LENGTH: 27
<212> TYPE: DNA
<213> ORGANISM: Artificial Sequence
<220> FEATURE:
<223> OTHER INFORMATION: IR-A62
<220> FEATURE:
<221> NAME/KEY: misc_feature
<222> LOCATION: (3)..(4)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (10)
<223> OTHER INFORMATION: 2-deoxyuridine which is modifed by hydrophobic
      group selected from the group consisting of benzyl, naphtyl,
      pyrrolbenzyl and tryptophanyl
```

```
<220> FEATURE:
<221> NAME/KEY: misc_feature
<222> LOCATION: (14)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (16)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (20)
<223> OTHER INFORMATION: 2-deoxyuridine which is modifed by hydrophobic
      group selected from the group consisting of benzyl, naphtyl,
      pyrrolbenzyl and tryptophanyl
<220> FEATURE:
<221> NAME/KEY: misc_feature
<222> LOCATION: (24)
<223> OTHER INFORMATION: 2-deoxyuridine which is modifed by hydrophobic
      group selected from the group consisting of benzyl, naphtyl,
      pyrrolbenzyl and tryptophanyl

<400> SEQUENCE: 7
cannacgcan gagncnagan ccgncag                                         27
```